United States Patent [19]

Haberman

[11] Patent Number: 5,188,959

[45] Date of Patent: Feb. 23, 1993

[54] EXTRACELLULAR MATRIX PROTEIN ADHERENT T CELLS

[75] Inventor: Allan B. Haberman, Somerville, Mass.

[73] Assignee: Trustees of Tufts College, Medford, Mass.

[21] Appl. No.: 525,512

[22] Filed: May 18, 1990

Related U.S. Application Data

[63] Continuation-in-part of Ser. No. 414,131, Sep. 28, 1989, abandoned.

[51] Int. Cl.$^5$ .......................... C12N 5/00; C12N 5/08; C12Q 1/04
[52] U.S. Cl. ............................ 435/240.243; 435/240.2; 435/4
[58] Field of Search ........... 435/240.1, 240.21, 240.23, 435/240.243, 240.2, 4

[56] References Cited

PUBLICATIONS

Brenner et al., Nature, v. 325, pp. 689-694, 1987.
Faure et al., The Journal of Immunology, v. 141, 3357-3360, 1988.
Takada et al., Journal of Cellular Biochemistry, v. 37, 385-393, 1988.
Hemler et al. (A), Journal of Biological Chemistry, v. 260, 15246-15252, 1985.
Hemler et al., (B), The Journal of Immunology, v. 138, 2941-2948, 1987.
Bucy, et al., "Tissue Localization and CD8 Accessory Molecule Expression of dg Cells in Humans", 1989, Jour. Immunol., vol. 142, pp. 3045-3049.
Falini, et al., "Distribution of T Cells Bearing Different Forms of the T Cell Receptor dg in Normal and Pathological Human Tissues", 1989, Jour. Immunol., vol. 143, pp. 2480-2488.
Goodman et al., "Expression of the dg T-Cell Receptor on Intestinal CD8+ Intraepithelial Lymphocytes", 1988, Nature, vol. 333, pp. 855-857.
Itohara, et al., "Homing of a dg Thymocyte Subset with Homogeneous T-Cell Receptors to Mucosal Epithelia", 1990, Nature, vol. 343, pp. 754-757.
Janeway, "Frontiers of the Immune System", 1988, Nature, vol. 333, pp. 804-806.
Maxfield, et al., "Murine T Cells Express A Cell Surface Receptor for Multiple Extracellular Matrix Proteins", 1989, Jour. Exp. Med., vol. 169, pp. 2173-2190.
Asarnow, "Limited Diversity of dg Antigen Receptor Genes of Thy-1+ Dendritic Epidermal Cells", 1988, Cell, vol. 55, pp. 837-847.
Band, et al., "Immunochemical Proof That a Novel Rearranging Gene Encodes the T Cell Receptor dg Subunit", 1987, Science, vol. 238, pp. 682-684.
Bluestone, et al., "TCR dg Cells–Minor Redundant T Cell Subset or Specialized Immune System Component?", 1989, Jour. Immunol., vol. 142, pp. 1785-1788.
Brenner, et al., "Identification of a Putative Second T-Cell Receptor", 1986, Nature, vol. 322, pp. 145-149.
Janeway, et al., "Specificity and Function of T Cells Bearing dg Receptors", 1988, Immunol. Today, vol. 9, pp. 73-76.
Duijvestijn, et al., "Mechanisms and Regulation of Lymphocyte Migration", 1989, Immunol. Today, vol. 10, pp. 23-ff.
MacKay, et al., "Naive and Memory T Cells Show Distinct Pathways of Lymphocyte Recirculation", 1990, Jour. Exp. Med., vol. 171, pp. 801-817.
Pitzalis, et al., "The Preferential Accumulation of Helper-Inducer T Lymphocytes in Inflammatory Lesions: Evidence for Regulation by Selective Endothelial and Homotypic Adhesion", 1988, Eur. J. Immunol., vol. 18, pp. 1397-1404.
Stoolman, "Adhesion Molecules Controlling Lymphocyte Migration", 1989, Cell, vol. 56, pp. 907-910.
Holzmann, et al., "Peyer's Patch-Specific Lymphocyte Homing Receptors Consist of a VLA-4-Like a Chain Associated with Either of Two Integrin b Chains, One of Which is Novel", 1989, EMBO Jour., vol. 8, pp. 1735-1741.
Elices, et al., "VCAM-1 on Activated Endothelium Interacts with the Leukocyte Integrin VLA-4 at a Site Distinct from the VLA-4/Fibronectin Binding Site", 1990, Cell, vol. 60, pp. 577-584.
Hemler, "VLA Proteins in the Integrin Family: Structures, Functions, and Their Role on Leukocytes", 1990, Ann. Rev. Immunol., vol. 8, pp. 365-400.

(List continued on next page.)

Primary Examiner—David L. Lacey
Assistant Examiner—George C. Elliott
Attorney, Agent, or Firm—Choate, Hall & Stewart

[57] ABSTRACT

Substantially purified mature T cells, including $\alpha\beta$ T cells and $\gamma\delta$ T cells, are capable of binding to an extracellular matrix protein, particularly to one or more of a collagen, a fibronectin, a laminin, a fibrinogen, or a proteoglycan. Also, compositions including the substantially purified ECM binding mature T cells, for use in adoptive immunotherapy in a subject. Also, methods for treating a condition in a mammal, including administering to the mammal an effective quantity of the substantially purified ECM binding mature T cells, and treatment methods using the compositions. Also, methods for increasing the proportion, in a cell population, of substantially purified ECM binding mature T cells. Also, a method for assessing the likelihood that a mixture of cells contains activated T cells capable of localizing to a site in vivo, wherein an extracellular matrix protein is present at the site, in which greater binding of T cells to an extracellular matrix protein on a support in vivo indicates a greater likelihood that a mixture of cells contains activated T cells capable of localizing to the site in vivo.

22 Claims, No Drawings

OTHER PUBLICATIONS

Hynes, "Integrins: A Family of Cell Surface Receptors", 1987, Cell, vol. 48, pp. 549-554.

Martin, "Laminin and Other Basement Membrane Components", 1987, Ann. Rev. Cell Biol., vol. 3, pp. 57-85.

Matsuyama, et al., "Activation of CD4 Cells by Fibronectin and Anti-CD3 Antibody", 1989, Jour. Exp. Med., vol. 170, pp. 1133-1148.

Ruoslahti, et al., "New Perspectives in Cell Adhesion: RGD and Integrins", 1987, Science, vol. 238, pp. 491-497.

Sanders, et al., "Human Memory T Lymphocytes Express Increased Levels of Three Cell Adhesion Molecules (LFA-3, CD2, and LFA-1) and Three Other Molecules (UCHL1, CDw29, and Pgp-1) and Have Enhanced IFN-d Production", 1988, Jour. Immunol., vol. 140, pp. 1401-1407.

Rosenberg, "Immunotherapy of Cancer Using Interleukin 2: Current Status and Future Prospects", 1988, Immunology Today, vol. 9, pp. 58-62.

Hercend, et al., "Characteristics and Uses of Natural Killer Cells", 1988, Immunology Today, vol. 9, pp. 291-293.

Muirhead, et al., "Flow Cytometry: Present and Future", 1985, Bio/Technology, vol. 3, pp. 337-356.

Dang, et al., "Human CD4 Helper T Cell Activation: Functional Involvement of Two Distinct Collagen Receptors, 1F7 and VLA Integrin Family", 1990, Jour. Exp. Med., vol. 172, pp. 649-ff.

Shimizu, et al., "Regulated Expression and Binding of Three VLA (b1) Integrin Receptors on T Cells" 1990, Nature, vol. 345, pp. 250-ff.

Shimizu, et al., "Roles of Adhesion Molecules in T-Cell Recognition: Fundamental Similarities between Four Integrins on Resting Human T Cells (LFA-1, VLA-4, VLA-5, VLA-6) in Expression, Binding, and Costimulation", 1990, Immunol. Rev., vol. 114, pp. 180-ff.

Shimizu, et al., "Lymphocyte Interactions with Extracellular Matrix", 1991, FASEB J., vol. 5, pp. 2292-2299.

EXTRACELLULAR MATRIX PROTEIN ADHERENT T CELLS

BACKGROUND OF THE INVENTION

This invention was made in the course of work supported in part by the United States Government, and the Government has certain rights in the invention.

This application is a Continuation-in-Part of my co-pending application U.S. Ser. No. 414,131, filed Sep. 28, 1989, now abandoned, hereby incorporated by reference.

This invention relates to isolation, identification and therapeutic use of populations of T cell lymphocytes, and particularly of populations of T cell lymphocytes that are capable of binding to specific extracellular matrix proteins.

The term "leukocyte" refers to any of the nucleated cells normally present in blood or tissues whose major function is defense against foreign invaders of the body. Our understanding today regarding the different types of leukocytes stems from the classic staining researches of Paul Ehrlich beginning in 1878 whose discovery of polychromatic and supravital stains led to the first important advances in the knowledge of leukocytes. His pioneer investigations based on the morphology of the different leukocytes coupled with the first understanding of the maturation sequence via the work of Pappenhein in 1914 led directly to the classification system used for decades thereafter. Initially, the different types of leukocytes were separated according to: (1) the type of defense function provided—i.e., phagocytosis, antibody production, or cellular immunity; (2) the shape of the nucleus of the cell—i.e., polymorphonuclear or mononuclear; (3) the site of origin for the cell—i.e., myeloid or lymphoid; and (4) the presence or absence of intracellular specific staining granules—i.e., granulocytes or non-granulocytes. This led directly to the identification and establishment of normal values of different types of leukocytes as neutrophils, eosinophils, basophils, monocytes (including macrophages), and lymphocytes. Of these five major leukocyte types, the lymphocyte (although first defined as a morphological entity in 1879) has since the early 1950's been the subject of major, intense, clinical, and research investigations which have led to unparalleled advances in our understanding of how these cells are created, organized, and function in vivo.

Lymphocytes are mononuclear cells whose cytoplasm does not contain any specific staining granules. As with other leukocytes and red blood cells, they originate in the bone marrow. Lymphocytes acquire their immunocompetence in the bone marrow and thymus, and reside in the organs of the peripheral lymphoid system (lymph nodes, spleen, adenoids and tonsils, the Peyer's patches of the small intestine) where they encounter antigens and mount immune responses. They also circulate in the peripheral blood; and may recirculate between the blood stream, the lymphoid organs, and sites of immune reactions in the tissues.

Lymphocytes have been divided broadly into two major orders: B-cells responsible for antibody production and the antibody (or humoral) immune response; and T cells responsible for cellular immune responses and immune regulation generally. In recent years the T cell lymphocyte has become ever more intensively explored.

In general, the present state of knowledge and understanding regarding T cell lymphocytes is based upon three different and complementary investigational approaches. These are, in summary: (a) study of the functional properties of T lymphocyte subsets; (b) study of the surface antigens found on T cells and their subsets, using specific monoclonal antibodies; and (c) use of the methods of biochemistry and molecular biology to investigate mechanisms of T cell functional activities and specificity. Because of the complexity of the immune system and the newness and rapidly changing nature of these modern immunological studies (e.g., most of the monoclonal antibodies which have made these studies possible were not available before the early 1980's), the results of these various studies can be difficult to understand and correlate. Therefore, the three approaches are discussed in greater detail below.

The first investigational basis is the functional designation resulting from an empirically observed in vivo and/or in vitro specific biological activity. Such observations provide functional designations including: helper/inducer T cell, cytotoxic/suppressor T cell, lymphokine activated killer cell, tumor infiltrating lymphocyte cell, delayed hypersensitivity cell, dendritic epidermal T cell, and intraepithelial lymphocyte (the latter two terms designating T cell subsets that can localize in particular areas of the body). Each of these describes an observed function of lymphocytes. The designations employed are solely in functional or operative terms because each identification is based exclusively on the observed capability or attributes of one type of T cell able to participate in specific biological activities and/or immunological events.

The second basis of T cell lymphocyte classification resulted from the ability to produce specific antibodies which are then employed to characterize and define the surface antigenic determinants or cell surface markers found on different kinds of T cell lymphocytes. With the ability to produce monoclonal antibodies such as the OKT series (produced by Ortho Diagnostic System, Inc.), the Leu series (produced by Beckon-Dickinson), and the Coulter series (produced by Coulter Immunology), the individual T cell antigenic designations for man, mouse, and other animals were created. In order to bring some order to the confusing alternative nomenclatures which have resulted from the development of various sets of monoclonal antibodies provided by different laboratories, a new nomenclature system was adopted by the First International Workshop on Human Leukocyte Differentiation Antigens (*Jour. Immunol.* 134:659-660 (1985); see also Knapp et al., *Immunol. Today* 10:253-258 (1989)]. Using this nomenclature system, all monoclonal antibodies that appear to detect a particular antigen are assigned to a numbered "cluster of differentiation" or "CD" for that antigen. It has been found that particular T cell subsets initially defined by function (such as helper and cytotoxic/suppressor T cells) also have characteristic cell surface markers as defined by specific monoclonal antibodies. The biochemical function of these cell surface markers is itself an active area of investigation. The phenotyping of the different T cells and their separation into different subclasses based on their individual surface markers has become the most favored investigational technique among researchers today.

The third investigational basis for identifying and distinguishing differences among the various populations comprising T cell lymphocytes involves molecular biological and molecular genetic studies of proteins involved in immunological activities of T cells, including recognition and responses to specific antigens. The focus of these studies is the T cell receptor which is responsible for the recognition of a specific antigen by that individual T cell.

T cell receptors ("TCR") on the classically defined types of cells such as helper and cytotoxic T cells were found to be composed of two subunits termed "TCR alpha and beta" proteins. These proteins are the specific products of individual genes that are themselves rearranged during thymic ontogeny (see, e.g., Allison et al., *Jour. Immunol.* 192:2293-2300 (1982); Meuer et al., *Jour. Exp. Med.* 157:705-719 (1983); Haskins et al., *Jour. Exp. Med.* 157:1149-1169 (1983)). These TCR alpha/-beta ("$\alpha\beta$") protein molecules are found to comodulate, to coimmunoprecipitate, and to be coexpressed with the CD3 glycoprotein; and the direct physical association of the two protein complexes was demonstrated by chemically cross-linking the TCR $\alpha\beta$ molecules to the CD3 glycoproteins. These $\alpha\beta$ T cell receptors do not recognize soluble antigens. Rather, they recognize antigens on cell surfaces, complexed with proteins of the major histocompatibility complex (or "MHC"). Moreover, the MHC protein must be of the correct "self" type (i.e., an MHC protein from the same individual organism or an organism genetically identical at that locus) as the T cell and not from a genetically different individual. The recognition of such antigens is thus said to be "MHC restricted". Helper T cells recognize antigens coupled with one class ("Class II") of MHC proteins on the surface of antigen-presenting cells such as macrophages; and the surface protein CD4 on the surface of these T cells is thought to serve as an accessory binding factor for the MHC protein. Cytotoxic T lymphocytes (or "CTL") recognize the surface antigens of their target cells when complexed with another class ("Class I") of the MHC proteins also found on the surface of the target cell. The surface protein CD8 on the CTL surface again is thought to serve as an accessory binding factor. Recognition of antigen results in a cascade of events within the T cell which leads to the expression of helper or cytotoxic functions. In the case of cytotoxicity, the CTL lyses its specific target cells. (For a general review of these processes, see the textbook by J. W. Kimball, "Introduction to Immunology," Second Edition, New York, MacMillan Publishing Company, 1986.)

More recently however, there has been an identification of a second T cell receptor protein complex directly associated and controlled by a different third and fourth gene designated gamma/delta (or "$\gamma\delta$") genes. These $\gamma\delta$ genes have been identified in the mouse and in man, and cells bearing $\gamma\delta$ TCRs constitute between 1 and 10% of peripheral T cells in both humans and mice. The present state of knowledge regarding the class of T cells carrying TCRs which are encoded by the $\gamma\delta$ genes is documented by the following representative publications: Brenner et al., *Nature* 322:145-149 (1986); Brenner et al., *Nature* 325:689-694 (1987); Faure et al., *Jour. Immunol.* 141:3357-3360 (1988); Janeway et al., *Immunol. Today* 9:73-76 (1988); Bluestone, J. and L. A. Matis, *Jour. Immunol.* 142:1785-1788 (1989); Band et al. *Science* 238:682-684 (1987); Janeway, C. A., *Nature* 333:804-806 (1988); and Hercend, T. and R. E. Schmidt, *Immunol. Today* 9:291-293 (1988).

In short, it is now clear that two lineages of T cells bearing the CD3 antigenic complex can be defined based upon the biochemical nature and presence of the heterodimeric receptor chains expressed as either $\alpha\beta$ proteins or $\gamma\delta$ proteins. The TCR $\alpha\beta$ T cells include the major classes of T cells with classic MHC-restricted helper, cytotoxic, and suppressor activities.

The function (or functions) of $\gamma\delta$ T cells is unknown. Gamma/delta T cells have been widely demonstrated to carry out non-MHC-restricted cytotoxic activity against a variety of tumor cells. However, this requires high concentrations of interleukin-2; and appears to be a lymphokine activated killer (or "LAK") phenomenon, a condition which can be demonstrated by $\alpha\beta$ T cells as well (see, e.g., Matis et al., *Nature* 330:262 (1987); Brooks, *Nature* 305:155 (1983); Shortman et al., *Curr. Topics. Microbiol. Immunol.* 116:111 (1986); Maziarz et al., Seventh Int. Congress Immunol., 1989, Abstract). Thus, the non-MHC-restricted cytotoxicity demonstrated by $\gamma\delta$ T cells may not be the usual physiological function(s) of these cells. Recent studies have demonstrated that at least some $\gamma\delta$ T cells can recognize MHC molecules; and in at least one case, recognize a specific antigen in an MHC-restricted manner (Bluestone et al., *Jour. Exp. Med.* 168:1899 (1988); Kozbor et al., *Jour. Exp. Med.* 169:1847 (1989)). In another laboratory, $\gamma\delta$ T cells have been isolated from the peripheral blood of patients with B cell lymphomas that can lyse their specific B cell lymphomas in vitro.

A particularly noteworthy feature of $\gamma\delta$ T cells is their localization in tissues. In the mouse, particular narrow classes of $\gamma\delta$ T cells have been shown to localize in the skin and intestinal epithelia (Asarnow et al., *Cell* 55:837 (1988); Goodman and Lefrancois, *Nature* 333:855 (1988)). No such localization in normal tissues has been found in the human (Groh et al., *Jour. Exp. Med.* 169:1277 (1989)); however, human $\gamma\delta$ T cells do appear to localize in various inflammatory sites. In the case of the human gut, although normal levels of $\gamma\delta$ T cells have been reported on the average to be low, they have also been reported to be significantly higher (17-33%) in the intestines of children with celiac disease (Russell et al., *FASEB Jour.* 3:A485 (1989); Spencer and Isaakson (letter) *Nature* 337:416 (1989)). Gamma/-delta T cells have been found in numbers somewhat higher than in blood in the synovial fluid and membranes of adult rheumatoid arthritis patients (Brennan et al., *Jour. Autoimmunity* 1:319 (1988)). Moreover, clones of $\gamma\delta$ T cells have been isolated from cerebrospinal fluid of patients with subacute sclerosing panencephalitis (Ang et al., *Jour. Exp. Med.* 165:1453-1458 (1987)) and from joint fluid of patients with juvenile rheumatoid arthritis (DeMaria et al., *Eur. Jour. Immunol.* 17:1815-1819 (1987)). In both humans and mice, $\gamma\delta$ T cells have been found to localize at anatomically distinct regions of the lymphoid system (Bucy et al., *Jour. Immunol.* 1412:2200 (1988)). In contrast, $\alpha\beta$ T cells constitute the bulk of the T cell populations in peripheral blood and peripheral lymph nodes, while $\gamma\delta$ T cells comprise at most a few percent. The basis of the ability of $\gamma\delta$ T cells to localize within tissues is at present unknown.

The true biological function and capability of TCR $\gamma\delta$ cells remains effectively unknown as has been explicitly noted in the literature (Bluestone, J. and L. A. Matis, *Jour. Immunol.* 142:1785-1788 (1989)). In addition, although great strides have been made in the last few years by defining the TCR $\gamma\delta$ cells in terms of their tissue distribution and protein receptor/gene organization format, the true physiological role and the potential receptor ligand for such TCR γδ cells remains elusive. Although much speculation and hope is placed upon future research investigations for TCR γδ cell populations, there is a continuing ignorance regarding methods for isolating such TCR γδ cells without using flow cytometry techniques and apparatus; and a continuing absence of knowledge or understanding of the attributes or potential uses and applications for individual populations of TCR γδ cells.

SUMMARY OF THE INVENTION

In general, in one aspect, the invention features substantially purified mature T cells capable of binding to an extracellular matrix protein, sometimes referred to herein as ECM binding T cells.

A cell "capable of binding to" an extracellular matrix protein, as that term is used herein, is a cell that, when suspended either in a "complex" adhesion medium (a standard culture medium containing serum and (if needed) an additional growth factor (such as, for example, IL-2) and either containing or not containing an extracellular matrix protein), or in a "simple" adhesion medium (RPMI serum-free cell culture medium lacking growth factors), and contacted with an extracellular matrix protein bound on a plastic culture plate surface, adheres to the surface strongly enough so that the cell is not detached by standard gentle pipetting or washing methods.

"Substantially purified T cells capable of binding to an extracellular matrix protein", as that term is used herein, means cells derived from a sample of T lymphocytes taken from a source animal that has a higher proportion of extracellular matrix protein binding T cells than are found in the source sample. A mixture of cell types can be "substantially purified" T cells capable of binding to an extracellular matrix protein, as that term is used herein, provided that cells in the mixture are capable in a standard binding assay, of greater binding (in terms of proportion of cells bound), reproducibly and to a statistically significant degree, to an extracellular matrix protein than to non-extracellular matrix proteins, such as BSA or ovalbumin. In such cell mixtures containing extracellular matrix protein-binding T cells that are capable of continuous long term growth, the mixture is "substantially purified" if the extracellular matrix protein-binding T cells constitute at the least a sufficient proportion of the cells in the mixture to display, without periodic reactivation, continuous long term growth through extended numbers of doublings, in serumized media or in media containing a serum substitute and any required growth factor such as, for example, IL-2.

In preferred embodiments, the ECM binding mature T cells include γδ T cells, or αβ T cells. "Gamma/delta" or "γδ" T cells means T cells that express γ and δ T cell receptors ("TCR"); and "alpha/beta" or "αβ" T cells means ells that express α and β TCR.

In some embodiments, the ECM binding mature T cells are capable of binding to a collagen such as, for example, collagen I or collagen IV; to fibronectin; to laminin; to fibrinogen; to a proteoglycan such as, for example, a glycosaminoglycan.

In another aspect, in general, the invention features a composition for use in adoptive immunotherapy in a subject animal, including the substantially purified ECM binding mature T cells in a pharmaceutically acceptable carrier for administration to the animal.

"Adoptive immunotherapy", as that term is used herein, means any treatment of a mammalian subject that entails transfer of living immune system cells into the subject. In addition to the T cells certain chemical agents that influence the immune response of the subject by, for example, potentiating the activity or the survival of the cells, or inhibiting immunosuppression, can be administered concurrently to the patient, and an adoptive immunotherapy composition according to the invention can include one or more such agents. The immune system cells for transfer can be derived from one or more source populations of cells removed from one or more animals; and all or a portion of the source cells can be removed from the subject being treated, or from another animal. Following removal from the donor or donors, the source cells are treated before transfer to the subject to change the behavior of the cells and/or to selectively alter the proportions of particular cell types and/or to expand their numbers.

In another aspect, in general, the invention features a method for treating a condition in a mammal, including administering to the mammal an effective quantity of the substantially purified ECM binding mature T cells.

In another aspect, in general, the invention features a method for treating a condition in a mammal, including administering to the mammal an adoptive immunotherapeutic composition containing ECM binding mature T cells.

In another aspect, in general, the invention features a method for increasing the proportion, in a cell population, of ECM binding mature T cells, including steps of providing a cell mixture containing activated T lymphocytes in a medium, contacting the activated T lymphocytes with an extracellular matrix protein on a support to permit at least a portion of the activated T lymphocytes to adhere to the extracellular matrix protein on the support, and separating the medium from the support together with any cells in the medium not adhering to the extracellular matrix protein on the support.

In preferred embodiments the step of providing a cell mixture containing activated T lymphocytes in a medium includes steps of contacting a cell mixture containing mononuclear leukocytes including T lymphocytes with a support, preferably a plastic support surface, to permit monocytes and macrophages present in the cell mixture to adhere to the support, and separating the support and any cells adhering to it from the cell mixture comprising T lymphocytes; the step of providing a cell mixture containing activated T lymphocytes includes steps of providing a cell mixture containing T lymphocytes and activating cells in the cell mixture; the step of providing a cell mixture including activated T lymphocytes further includes the step of activating cells in the cell mixture; the cell activating step includes contacting the cell mixture with a first lymphokine-containing medium; the cell mixture containing T lymphocytes includes cells derived from a first source animal, and the activating step includes contacting the cell mixture with lymphocytes derived from a second source animal; the lymphocytes derived from the second source animal include irradiated lymphocytes; the activating step includes contacting the cell mixture containing T lymphocytes with a lectin and with irradiated peripheral blood mononuclear cells; the activating step includes contacting the cell mixture containing T lymphocytes with mixed B lymphoblastoid cells (preferably EBV-transformed) either alone or some combination of irradiated heterologous peripheral blood lymphocytes and/or a lectin and/or indomethacin; the irradiated peripheral blood mononuclear cells and at least a portion of the cell mixture containing T lymphocytes are derived from the same source animal; at least a portion of the cell mixture containing T lymphocytes is derived from a first source animal, and the irradiated peripheral blood mononucleocytes are derived from a second source animal; the activating step includes contacting the cell mixture containing T lymphocytes with a mitogenic antibody, preferably a monoclonal antibody, more preferably an anti-CD2, anti-CD3, or an anti-T cell receptor monoclonal antibody; the contacting step includes contacting the cell mixture containing T lymphocytes with an extracellular matrix protein different in composition from the extracellular matrix protein on the support; the contacting step includes contacting the cell mixture containing T lymphocytes with an extracellular matrix protein on a support and to a mitogenic antibody; the extracellular matrix protein on the support is a collagen in any of its forms, including collagen IV, laminin, heparan sulfate proteoglycans, nidogen/entactin, BM-40/SPARC/bone osteonectin, a glycosaminoglycan, and fibronectin; the extracellular matrix protein different from the extracellular matrix protein on the support is a collagen in any of its forms, including collagen IV, laminin, heparan sulfate proteoglycans, nidogen/entactin, BM-40/SPARC/bone osteonectin, a glycosaminoglycan, and fibronectin; the lymphokine in the first lymphokine-containing medium includes an interleukin, such as interleukin-2, or interleukin-4; the lymphokine in the first lymphokine-containing medium is tumor necrosis factor, granulocyte macrophage colony stimulating factor, or γ interferon.

In another aspect, in general, the invention features a method for assessing the likelihood that a mixture of cells contains activated T cells capable of localizing in vivo to a site at which an extracellular matrix protein is present, including steps of contacting the mixture of cells with the extracellular matrix protein on a support, under conditions that permit binding to the extracellular matrix protein on a support of T cells that are capable of binding to the extracellular matrix protein, whereby greater binding of T cells from the mixture to the extracellular matrix protein on the support indicates a greater likelihood that the mixture of cells contains activated T cells capable of localizing to the site in vivo.

DESCRIPTION OF THE PREFERRED EMBODIMENTS

The present invention is concerned with a specific populations of T cell lymphocytes; methods for the isolation of these particular populations; and therapeutic methods for using such populations of T cells for adoptive immunotherapy in the treatment of different kinds of cancer. By the historical development of this scientific area and via the disparity of investigational techniques and biochemical mechanisms of actions proposed over the last century concerning lymphocytes in general, the user must have: a thorough and detailed grounding and understanding of the publishing literature particularly over the last fifteen years; and a familiarity and in-depth comprehension of the various investigational assays, reagents, techniques, and apparatus presently employed to identify and distinguish among different populations of T cell lymphocytes. The complexity, newness, and rapidly changing nature of modern immunological investigations have resulted in the failure to provide precise terms and nonambiguous nomenclature, especially as different laboratories adapt older, existing terminology to fit new observations. For this reason, a focused and precisely articulated series of definitions are provided hereinafter which will serve as the sole and exclusive basis of definition and terminology throughout the entire detailed disclosure of the present invention. In addition, in so far as is reasonable or plausible, sufficient details regarding characteristics, attributes, and capabilities, along with such reference citations as are appropriate, will be provided whenever possible.

I. Nomenclature and Definitions

The CD Cluster Designation of Antigenic Cell Surface Markers

The CD cluster designation series has been defined by the First International Workshop On Human Leukocyte Differentiation Antigens and has come into general use as the nomenclature to be employed with detection of cell surface antigens for the classification of mammalian lymphocytes generally. The CD cluster designation is thus synonymous with any proper designation for the "T series" of surface markers in human lymphocytes and the "Ly series", L3T4, etc. of designations typically employed with murine lymphocytes. In so far as is possible, only the CD cluster designations will be employed herein; and the CD designation will be recognized as a proper substitute and replacement for both the T series and the Ly series, L3T4 etc., as individually known. Accordingly, all mature T cell lymphocytes must be CD3+ as determined by specific monoclonal antibodies. Similarly, the former "T4+" cells will now be designated as CD4+; and the former "T8+" cells will now be designated as CD8+ cells exclusively. A general representation of the overlap of CD designations with former terms is provided by Tables I and II respectively hereinafter.

Lymphokines

These are biologically active substances (such as interleukin-2, gamma-interferon, etc.) secreted by various types of lymphocytes, especially activated T lymphocytes. Other biologically active substances in the immune system, notably interleukin-1, are secreted by monocytes and macrophages, and are often known as monokines. The distinction between lymphokines and monokines is confusing; for example, interleukin-1 while normally considered a monokine can be secreted by certain T cells as well as by macrophages (Tartakovsky et al., *Jour. Immunol* 141:3863 (1988)). For this reason, the term "lymphokine" will be used to refer to both classes of regulatory molecules.

Different types of lymphokines exert their effects on various classes of immune cells (monocyte/macrophages, T cells, B-cells) and even on other cell types such as endothelial cells in blood vessel walls, fibroblasts, and, in the case of fever mediated by IL-1, the nervous system. Lymphokine action on immune cells is in part responsible for antigen-specific activation and immune responses. A representative listing of lymphokines which are either synthesized by or regulate T cells is provided by Table III below. The usual lymphokine which is used to support the proliferation of activated T cells in culture (including TILs), as well as to induce LAK activity in subsets of T cells and NK cells, is IL-2. However, IL-4 has recently been used, either alone or in combination with IL-2, to support the growth of activated T cells and in particular to support the expansion of TILs from tumor samples (Kawakami et al., Jour. Exp. Med. 168:2183 (1988); Spits et al., Jour. Immunol 139:1142 (1987)). IL-4 when added to human peripheral blood lymphocytes, either alone or in combination with IL-2, suppresses the induction of LAK activity. However, when added to a LAK culture previously established in the presence of IL-2, the IL-4 does not affect the cell's cytolytic activity, but does promote the continued growth of the T cells (Spits et al., Jour. Immunol. 141:29 (1988)). As listed in Table III, other lymphokines (notably interleukins-1 and -6) may also be involved—especially in combination with other lymphokines and/or accessory cells in the growth of T cells.

TABLE I

| CLUSTER DESIGNATION | WORKSHOP ANTIBODIES | TYPICAL LEUKOCYTE SUBPOPULATIONS | LEUKOCYTE MALIGNANCIES |
|---|---|---|---|
| CD1 (Thy, p 45,12) | NA1/34,T6,M241,D47 | Corticothymocytes | Few T-All and T-LL |
| CD2 (T, p 50) | 9.6,Til,35.1 | All T-cells forming E rosette | Most T-cell malignancies |
| CD3 (T, p 19-29) | T3,UCHT1,89b1,38.1 | Mature T-cells | Most T-CLL & CTCL, few T-ALL and T-LL |
| CD4 (T, p 55) | T4,Leu3a,91D6 | Subset T-cells, mostly inducers | Few T-All, some T-CLL, all CTCL |
| CD5 (T, p 67) | A50,10.2,Ti,UCHT2,SCI, AMG4,T101,Crisl,H65, HH9 | Pan T + subpopulation B cells | Most T-cell malignancies, some B-CLL |
| CD6 (T, p 120) | 12.1,T411,B614,WT31, MBG6 | Mature T + subpopulation B cells | Few T-ALL, most T-CLL & CTCL, some B-CLL |
| CD7 (T, p 41) | 3AL,4A,CL1.3 | Pan T | Most T-All, some T-CLL & few CTCL |
| CD8 (T, p 32-33) | Leu2a,TB,M236,51.1, UCHT4, 2D2, B9.4.1, B9.3.1,B9.7.6,B9.2.4, B9.8.6,B9.11.10, B9.1.1,C10,T811 | Subset of T-cells, mostly cytotoxic/ suppressor | Few T-ALL & T-CLL |
| CD9 (nT,nB, p 24) | BA2,DU-ALL-1,FMC8, SJ9A-4,WB3 | Monocytes | Most non-T-non-B ALL, few B-CLL |
| CD10 (nT,nB, p 100) | J5,BA3,NL-1,24.1, VIL-AL | Pre-B cell polymorphs | Most non-T-non-B ALL |
| CD11 (M,G,u) | Mol,B2.12,M522 | Monocytes and granulocytes, some bone marrow cells | Some M4 and most M5 stages of AML some CML |
| CDw12 (M,G,u) | 20.2,M67 | Monocytes and granulocytes | Few M4 and M5 stages of AML |
| CDw13 (M,G,u) | MY7,DU-HL60-4,MCS.2 | Monocytes and granulocytes | Most M1 and few M4 or M5 stages of AML some CML |
| CDw14 (M,u) | 20.3,5F1,MOP15,M02, MOS1,MY4,MOS30,TM18, MOP9,FMC17 | Monocytes | Few M4 & some M5 stages of AML |
| CDw15 (G,u) | BOH3,B13.9,MCS.1,82H7 FMC12,FMC13,WM37, DU-HL-60.1,FMC10,WM27, WM30,G1120,TG8,WM38, TG1,DU-HL60-3,G2,B4.3, VIMD5,WV41,IGL0 | Granulocytes, some bone marrow cells | Most M4 and some M5 stages of AML, some CML |

TABLE II

| ANTIGENS | MOLECULAR WEIGHT* | MONOCLONAL ANTIBODY | PERCENT POSITIVE | | COMMENTS |
| | | | THYMO-CYTES | PERIPHERAL T-CELLS | |
|---|---|---|---|---|---|
| T11 (CD1) | 55,000 | OKT 11 Leu 5 | 95 | 100 | associated with SRBC rosette receptor |
| T10 | 37,000 | OKT 10 | 95 | 5 | Present on early stem cells, some B cells, activated peripheral T-cells |
| T9 | 190,000 | OKT 9 | 10 | 0 | Transferrin receptor, present on activated T-cells |
| T8 (CD8) | 32,000 43,000 | OKT 8 Leu 2a Leu 2b | 80 | 35 | Present on cytotoxic/ suppressor cells |
| T6 (CD1) | 44,000 | OKT 6 Leu 6 | 70 | 0 | Equivalent to murine TL antigen |
| T4 (CD4) | 60,000 | OKT 4 Leu 3 | 75 | 65 | Present on helper/ inducer T-cells |
| T3 (CD3) | 20,000 23,000 26,000 | OKT 3 Leu 4 | 20 | 100 | Associated with the T-cell receptor for antigen |
| T1 (CD5) | 67,000 | OKT 1 | 95 | 100 | Equivalent to |

TABLE II-continued

| ANTIGENS | MOLECULAR WEIGHT* | MONOCLONAL ANTIBODY | PERCENT POSITIVE | | COMMENTS |
|---|---|---|---|---|---|
| | | | THYMO-CYTES | PERIPHERAL T-CELLS | |
| | | Leu 1 | | | murine Ly-1 antigen |

TABLE III

| LYMPHOKINES | ACTION (partial description) |
|---|---|
| Interleukin-1 (IL-1) | Involved in activation of resting T cells |
| Interleukin-2 (IL-2) | Proliferation of T cells; induction of LAK activity in susceptible natural killer and T cells |
| Interleukin-3 (IL-3) | Proliferation of mast cells and granulocytes |
| Interleukin-4 (IL-4) | Proliferation, activation, and differentiation of B-cells, T cells, and NKs; inhibits human LAK activity; augments growth of specific TILs in low-dose IL-2 |
| Interleukin-6 (IL-6) | Growth and differentiation of B-cells and T cells |
| Tumor necrosis factor (TNF) | Cytotoxic for some tumor cells; involved in activation of blood vessel endothelial cells |
| Granulocyte macrophage colony stimulating factor (GM-CSF) | Involved in differentiation of granulocytes and monocyte/macrophages; stimulates antigen presenting activity of macrophages |
| Gamma interferon | Stimulates expression of MHC class II proteins on surface of macrophages, some tumor cells, etc.; stimulates antigen presenting activity of macrophages |

T Cell Lymphocytes

T cell precursors originate in the bone marrow; and the vast majority of T cells mature in the thymus. A key event in this maturation is the rearrangement and expression of the TCR gene. Mature T cells are present in peripheral blood, lymphoid organs other than thymus and bone marrow, in inflammatory sites, and to a lesser extent in tissues. All mature T cells must demonstrate CD3+ determinants and TCR $\alpha\beta$ or $\gamma\delta$ receptor proteins. Other cell surface antigenic markers (determinants) may or may not be present. The majority of mature T cells are CD4+CD8−, or CD8+CD4−; minority populations of cells which are double negative or double positive for CD4 and CD8 also exist.

NK or Natural Killer Cells

All NK or natural killer cells are CD3− and TCR−, i.e., negative for both $\alpha\beta$ and $\gamma\delta$ receptor proteins. NK cells often appear as large granular lymphocytes morphologically; and they commonly express cell surface markers such as CD16+ and Leu19+ (NKH-1+; recently assigned to CD56) in the case of human NKs. Natural killer cells mediate cytolytic actions which do not require the presence or expression of specific Class I or Class II MHC antigens on the target cells and are accordingly deemed non-MHC restricted per se (Hercend, T. and R. E. Schmidt, Immunology Today 9:291 (1988)). The known target cells which are sensitive to NK cytolytic activity presently represent a limited number of in vitro established leukemia cell lines, the classic one being K562 cells. It should be noted also that NK cells are different and distinguishable from certain populations of T cell lymphocytes which are CD3+. Mature T cells are either $\alpha\beta$ receptor or $\gamma\delta$ receptor positive; and may demonstrate, particularly upon activation and culture in medium containing high concentrations of IL-2, a non-MHC restricted cytolytic activity which resembles the activity of natural killer cells. T cells which exhibit such an activity may also express Leu19. The published scientific literature has on occasion called such T cells "NK-like" cells or cells having "NK-like activity". These terms will *not* be employed at any time herein Rather, only the strict definition and meaning as stated above for NK cells will be employed.

CTL or Cytotoxic T Lymphocytes

All CTL cells demonstrate MHC-restricted cytotoxicity against target cells. By definition, therefore, CTL cells all recognize a specific antigen within the context of a specific MHC Class I or Class II antigen on the surface of a target cell before lysis of the cell can occur. Accordingly, the CTL cell is defined by: (a) rearrangement and competent transcription of genes for the T cell receptor ("TCR") protein, or "Ti" complex, i.e., the Ti genes; (b) expression of the CD3/Ti complex on the cell surface; and (c) cytolytic function that is antigen-specific and MHC restricted (Lanier, L. and J. H. Phillips, Immunology Today 5:132 (1986)). This population of cells is different and is to be distinguished from non-MHC-restricted cytotoxic cells.

Non-MHC Restricted Cytotoxic Lymphocytes

Certain T lymphocytes may express non-MHC restricted cytotoxic activity. Such cells may be $\alpha\beta$ or $\gamma\delta$. They include minority populations of T cells from peripheral blood and tissues which display such activity; as well as other T cell subsets which display this activity when activated and cultured in media containing large concentrations of IL-2. This type of T cell is defined by: (a) rearrangement of Ti genes; (b) expression of CD3/Ti on the cell surface; and (c) cytotoxic function that is not restricted by the MHC antigenic markers. It is noteworthy that this type of CD3+ cytolytic cell has improperly been referred to in the literature as a "NK" cell because it is capable of lysing natural killer sensitive target cells without any requirement for MHC antigen restriction. This designation and terminology is not correct; these cells should be referred to as T cells displaying non-MHC restricted cytolytic activity (or, LAK activity, if they display such activity for a wide variety of tumor cells after lymphokine activation) (Lanier, L. and J. H. Philips, Immunology Today 7:132 (1986)). There is evidence that T cells with a known MHC restricted function may be induced to carry out non-MHC restricted cytotoxic activity (Matic et al., Nature 330:262 (1987); Brooks, Nature 305:155 (1983); Shortman et al., Curr. To. Microbiol. Immunol. 116:111 (1986); Maziarz et al., 1989, Seventh Int. Congress Immunol., Abstract); and that the TCR determinant of T cells displaying non-MHC specific activity may not even be involved in that activity (Spits et al., Eur. Jour. Immunol. 15:88 (1985); Phillips et al., Jour. Exp. Med. 166:1579 (1989)). It is therefore possible that T cells displaying non-MHC specific cytotoxic activity may, in addition, have MHC-restricted, TCR-dependent activities as well. The major differences between classical CTL cells, NK cells, and T cells displaying non-MHC restricted activity are represented by the information within Table IV.

TABLE IV

| PROPERTIES | MHC RESTRICTED CTL | NON-MHC RESTRICTED CTL | NK CELL |
|---|---|---|---|
| CD3/Ti | Yes | Yes | No |
| CD2/E receptor | Yes | Yes | Yes |
| CD4 | Yes (subset) Class II restricted | Usually No | No |
| CD8 | Yes Class I restricted | Yes | Yes (subset) |
| Fc (CD16) receptor/ ADCC function | Usually no | Usually no | Yes |
| Leu19/NKH-1/ (CD56) | No | Usually yes | Yes |
| Cytotoxicity Inhibited by: | | | |
| Anti-CD2 | Yes | Yes | No |
| Anti-CD4 | Yes (some) | No | No |
| Anti CD8 | Yes (some) | No | No |
| Anti-LFA-1 | Yes | Yes | Yes |
| Anti-CD3 | Yes | Yes | No |
| Specific Anti-TCR Clonotype Antibody | Yes | Yes | No |
| "LGL" morphology | Yes (some) | Yes | Yes |
| Origin | Thymic | Thymic | Bone marrow |

TCR Or T Cell Receptor

This is the antigenically and biochemically recognized protein complex on the surface of all mature T cell lymphocytes which is found complexed with CD3+ protein and which determines the specificity of the T cell for a specific antigen The TCR protein complex (or "Ti" complex) typically binds or is associated with a specific antigen within the context of a specific MHC molecule as discussed above. Depending upon which individual protein components are associated with the TCR molecule, the individual cell may be either an alpha/beta ($\alpha\beta$) TCR or a gamma/delta ($\gamma\delta$) TCR protein complex. The vast majority of T cells circulating within normal peripheral blood, lymph nodes, and spleen are $\alpha\beta$ T cell receptor proteins; only about 1-10% of T cell lymphocytes in normal blood circulation are $\gamma\delta$ TCR cells. Conversely, there is substantial evidence that the majority of T cells found within at least certain epithelial tissues in the mouse are $\gamma\delta$ cells (Janeway, C. A., *Nature* 333:804 (1988)). The TCR protein is also known as the "Ti" complex.

Other T Cell Surface Markers

Some of the other well recognized and functionally associated T cell surface markers or receptor proteins are those which have now been well defined by the use of specific monoclonal antibodies. These include the CD4+ marker also known as the T4+ marker on the human cell which is classically associated with helper-/inducer T cell function. Such CD4+ cells are believed to be important for accessory binding in that the CD4 protein strengthens the binding of the TCR protein to a specific antigen and the MHC Class II on an antigen-presenting cell. In addition, the CD8+ (or human T8+) marker has been classically associated with both suppressor T cells and cytotoxic T lymphocytes in vivo. Such CD8+ classically exhibit MHC-restricted cytotoxicity in that they recognize a specific antigen in the context of a specific MHC Class I determinant on the surface of a target cell with subsequent lysis of the target. Some T cells have been identified which are lacking both CD4 and CD8 receptor markers and are therefore said to be "double negative" or "DN" cells Conversely, many populations of tumor infiltrating lymphocytes or "TIL" contain subpopulations which demonstrate both CD4+ and CD8+ surface markers and are accordingly termed "double positive" T cell lymphocytes. Finally, another major cell surface receptor marker is the Leu19 (recently assigned to CD56) determinant found on many kinds of T cells and NK cells which exhibit non-MHC restricted cytotoxicity.

TIL or Tumor Infiltrating Lymphocytes

These are T cell lymphocytes which are derived from growing resected human or animal *solid tumors* in culture medium and subsequently isolating the lymphocytes from the in vitro cultured tumor tissue. This definition therefore is exclusively an operational or functional definition by which the obtained lymphocytes are recognized as in vitro obtained cells originating from a solid tumor source alone. When such solid tumors are treated by various disassociation methods (Topalian et. al., *Jour. Immunol. Methods* 102:127 (1987); Kurnick et al., *Clin. Immunol. Immunopathol.* 38:367 (1986)) and cultured in a lymphokine containing media (such as with IL-2), the resulting TIL population obtained in this manner may be expanded in size and maintained under in vitro conditions. Such TIL cells typically are almost entirely T cell lymphocytes demonstrating CD3+ surface markers; and often demonstrate cytolytic activities which can be specific for the individual tumor tissue and tumor cells from which they were originally derived. TILs are thus complex mixtures of T cells which can contain various proportions of cells. (from 0–100%) which are CD4+, CD8+, double negative (CD4− and CD8−), or double positive (CD4+ and CD8+). They may also contain subpopulations displaying the Leu19 marker (Rosenberg, S. A., *Immunology Today* 9:58 (1988) and the reference cited therein). Note that production of TILs requires treatment with a lymphokine such as IL-2; and that TILs obtained in this manner may display specific cytotoxic activity against the tumor from which they were derived and/or provided "LAK activity" as defined below.

LAK or Lymphokine Activated Killer Cells

LAK cells are by definition lymphokine activated (usually using interleukin-2) and can be derived by lymphokine induction of either NK cell or T cell types. A LAK cell is thus only an operational/functional definition in which the particular activated cell or cell population displays non-MHC restricted cytotoxic activity for a wider variety of cell targets and cell types than that usually displayed by NK cells or by non-lymphokine treated T cells displaying non-MHC restricted cytolytic activity. Such cytolytic activity has been termed "LAK activity" classically because it is determined empirically by measuring cytolytic activity with an NK-insensitive target cell such as Daudi cells. The "LAK phenomenon" results when lymphocytes, either from the peripheral blood or from the solid tissues, are cultured in vitro with lymphokine containing culture media; and thereby acquire the ability to lyse a wider variety of cell types than before treatment with the lymphokine. This operational definition of LAK cells inherently recognizes an empirical cell activation and induction of cytolytic activity; but does *not* include or provide any information regarding either the presence or absence of the TCR protein complex or the individual CD surface markers originally present (Rosenberg, S. A., *Immunology Today* 9:58 (1988); Hercend and Schmidt, *Immunology Today* 9:291 (1988)).

Operationally, the "LAK cells" or "LAK cultures" used in LAK therapy are peripheral blood lymphocytes initially cultured in IL-2 containing media, which subsequently display LAK activity. The majority of cells displaying such activity in these cultures are of the NK lineage, although both $\alpha\beta$ T cells and $\gamma\delta$ T cells with LAK activity are typically present in these LAK cultures.

Extracellular Matrix ("ECM") and Their Components, Including ECM Proteins and Basement Membranes and Their Components Basement membranes comprise a class of extracellular matrix ("ECM") material that is of particular significance for localization by lymphocytes; and basement membrane proteins comprise a class of extracellular matrix proteins, that play a significant role in lymphocyte localization. Extracellular matrices are insoluble meshworks of proteins and carbohydrates which fill most of the intracellular spaces in the body (Ruoslahti and Pierschbacher, *Science* 238:492 (1987)). Matrices of various types are found in different locations in the body; and typically are formed of diverse combinations of collagens, proteoglycans, elastin, hyaluronic acid, and various glycoproteins including laminin and fibronectin. Cells of different types interact with nearly all of the extracellular matrix glycoproteins and collagens which have been identified to date. Such interactions can result in adhesion, spreading, migration, growth, and differentiation of cells involved. Basement membranes are the thin extracellular matrices which surround epithelial tissues, the outside of endothelial cells in capilaries and other blood vessels, nerves, fat cells, muscle, and other cell types (Martin and Timpl, *Ann. Rev. Cell Biol.* 3:57 (1987)). Basement membranes create barriers in vivo which allow embryonic cells and tissues to segregate and differentiate. They also provide the in vivo scaffolding that maintains normal tissue form and serve as molecular filters in kidney glomeruli and in capillaries to prevent passage of proteins. With respect to immune cells, the basement membranes constitute barriers to passage of lymphocytes and other leukocytes out of the bloodstream and into lymph nodes, inflammatory sites, tumors, and other actual or potential sites of immune action in the tissues of the body. Lymphocytes which are able to target and migrate towards such sites must therefore possess the capacity to traverse these blood vessel basement membrane barriers at the individual site of action. With respect to tumor cells, tissue basement membranes constitute barriers which metastasizing tumor cells must be able to traverse in order to establish metastases. As with other extracellular matrices, basement membranes are also involved in the adhesion, migration, growth, and differentiation of specific cell types.

The two major components of basement membranes are collagen IV and laminin. Other components include heparan sulfate proteoglycan, nidogen (also known as entactin), and minor components (which may be variable in different basement membranes in the body) including SPARC/bone osteonectin and fibronectin. By definition, therefore, any protein which can be isolated from a basement membrane in vivo or in vitro is deemed to be a member of this class of protein. Accordingly, the common components found in all basement membranes as well as those compositions found specifically in basement membranes within particular tissues are all members of this class.

II. Overview Of The Present Invention

It will be recognized and appreciated that presently known methods for the detection, enumeration, and isolation of $\gamma\delta$ T cell lymphocytes depend upon the use of two individual methods and techniques. These are: (1) the empirical finding that the vast majority of double negative peripheral blood T cells are presumptively $\gamma\delta$ TCR cells based upon biochemical analysis of the proteins and/or RNA expression, DNA rearrangement, and the like (Bank et al., *Nature* 322:179 (1986); Brenner et al., *Nature* 322:145 (1986); Rivas et al., *Jour. Immunol.* 142:1840 (1989)). To identify these cells, the user employs specific fluorescent-labelled monoclonal antibody stains for the CD3, CD4, and CD8 surface proteins; and then utilizes the conventionally known apparatus and techniques of flow cytometry to isolate the double negative cells (Muirhead et al., *Bio/Technology* 3:337-356 (1985) and references cited therein). Those cells which are CD3+ but are also CD4− and CD8− (double negative) are presumptively believed to be $\gamma\delta$ cells.

In the alternative technique, the user employs specific monoclonal antibodies for the TCR protein complex—notably WT31 antibody specific for the $\alpha\beta$ receptor protein or the very recently developed anti-delta reagent, TCR$\delta$1 (Brenner et al., *Nature* 325:689 (1987) and references cited therein; Faure et al., *Jour. Immunol.* 141:3357-3360 (1988) and references cited therein). Using this technique, the investigator either stains the cells with WT31 antibody and sorts out the cell population for WT31− cells; or specifically stains the cells with TCR$\delta$1 antibody and sorts the stained population for the presence of TCR$\delta$1+ T cells. In the latter methodology, the apparatus and techniques of flow cytometry are also of maximum value for accuracy and speed of accomplishment; and, indeed, are essential for the separation of cells on the basis of their labelling with the fluorescent-labelled antibodies.

This population consists of adhesive $\gamma\delta$ T cells, and in the case of EMATs (described below) represents approximately 5-10% of all peripheral blood $\gamma\delta$ T cells and unknown proportions of tissue $\gamma\delta$ T cells in the human. The activation/adhesion methods do not in all circumstances result in $\gamma\delta$ T cells; for instance activation of PBL in the presence of a recall antigen followed by fibronectin binding may yield memory T cells, which will include mainly helper T CD4+ and cytotoxic T CD8+ TCR$\alpha\beta$ cells, as discussed more fully below. And, also as discussed more fully below, I have discovered $\alpha\beta$ T cells in the EMAT population, which are specific adherent T cells.

It will be recognized and appreciated therefore, that the present invention is a major departure and deviation from the conventionally known methods, techniques, and apparatus for presumptively identifying and/or isolating presumptive $\gamma\delta$ cells and populations. The methodology of the present invention also provides a number of unique advantages and achievements which were previously unknown and unavailable to practitioners ordinarily skilled in this art. These include:

1. An ability to identify and isolate an individual population of γδ receptor T cell lymphocytes based on their functional characteristics and properties alone. If the user subsequently wishes to characterize the isolated population obtained after using the methods of the present invention, the user is free to do so using either the conventionally known molecular, biochemical, or monoclonal antibody techniques to identify the various known cell surface markers. As will be noted hereinafter within the experimental data provided, the confirmatory evidence establishes such cell characteristics for various isolated populations. Nevertheless, such confirmatory procedures are deemed optional and thus a matter of mere convenience to the individual user.

2. The present methodology does not utilize or require flow cytometry apparatus or techniques whatsoever for the actual isolation and maintenance of the cell populations.

3. The present methodology provides a means of isolating and characterizing γδ T cell subpopulations on the basis of their specific adhesive properties. Current methods are dependent on characterization and the basis of specific TCR monoclonal antibodies, biochemical and molecular methods for distinguishing different types of TCR proteins; their location in the body (in the case especially of murine epidermal and gut γδ T cell populations); and, in a few cases, their identification based on their reactivity to specific antigens.

Since the physiological functions of γδ T cells are unknown, it is most desirable to have this novel means of isolating specific γδ T cell subpopulations on the basis of this important adhesion property. The invention additionally provides a means for characterizing αβ subpopulations on the basis of functional characteristics which are expected to be related to localization, activation, and function.

A. Obtaining A Mixture Of T Cell Lymphocytes

Initially, one obtains a mixture of T cell lymphocytes as the basis for isolating the population comprising specifically adherent T cells. For purposes of the present invention, the source of T cell lymphocytes is neither essential nor critical so long as it is a cell population which comprises a proportion of T cells—a percentage of which presumptively includes specifically adherent subpopulations. Accordingly, the source may be: peripheral blood leukocytes taken ex vivo from a living subject; or spleen, lymph node, thymus, or other lymphoid tissue; or a mixed population of leukocytes including lymphocytes which have been maintained under in vitro conditions; or tissue samples believed to contain or supply activatable and/or activated T lymphocytes such as tumor tissue as a source of TIL cells; or any other resource of origin wherein the mixture of cells includes mononuclear leukocytes of which at least some demonstrate the presence of the CD3+ surface antigen. It is clear therefore that the sole requirements as to source are that some recognizable T cells as such exist in the material; and a good faith belief that some proportion of these T cells be specifically adherent T cells. Conversely, there are no other essential demands or requirements whatsoever for the cellular mixture comprising the raw material.

It is most desirable, however, that the mixture of cells be prepared to consist primarily, if not exclusively, of T cell lymphocytes. For example, if the source material is fresh peripheral blood taken from a living subject, it is useful to first isolate mononuclear cells from the whole blood and Ficoll Hypaque media using conventionally known methods (A. Boyum, *Scand. Jour. Clin. Lab. Invest.* 21:(Suppl. 97) (1968)). It is also very desirable to deplete peripheral blood mononuclear cells of monocytes and macrophages using conventionally known methods, as for example, by incubation of the cells in serum containing medium in tissue culture plastic flasks and removing the cells which adhere to the plastic surface (Mosier, *Methods in Enzymology* 108:294 (1984); Maizel et al., *Cellular Immunol.* 28:383 (1979)). In this preferred method, peripheral blood mononuclear cells are resuspended (at preferably a concentration of $10^6$ cells per milliliter) in a suitable lymphocyte supporting culture medium such as LAK medium (comprising RPMI 1640 medium containing 10% heat inactivated human serum, penicillin (100 units/ml), and streptomycin (100 mg/ml) in plastic T75 culture flasks. By maintaining the mixture of mononuclear leukocytes within the culture medium in the presence of the plastic solid surface comprising the wall of the T75 culture flask, the vast majority of such monocytes and macrophages as are present in the cellular mixture become adhered to the plastic solid surface of the flask; while the majority of such lymphocytes as are present in the mixture remain non-adherent and suspended within the LAK culture medium contained within the T75 culture flask. Preferably, the T75 flasks are incubated, flat side down, at 37° C. for about one hour in order to ensure that the monocytes and macrophages become adherent to the plastic. Subsequently, the non-adherent cells suspended within the fluid medium are pipetted from the flask and centrifuged at about 1,500 rpm for approximately 10 minutes in a cell culture centrifuge to concentrate the cells then remaining. The resulting cell mixture is composed almost entirely of T cells, NK cells, and B-cells. The B-cells, however, are incapable of either growth or activation using the described culture methods and will die during the first few days of culture.

B. Preparing A LAK Culture From The Lymphocyte Mixture

Once the mixture of lymphocytes has been obtained and preferably concentrated, this mixture is then to be activated and prepared as a LAK culture (i.e., a culture of lymphocytes incubated in a medium containing one or more lymphokines such as IL-2 which will result in the induction of LAK activity). This is preferably performed by suspending the mixture of T cell lymphocytes (desirably at a concentration of about $2 \times 10^6$ per milliliter) in a lymphocyte supporting medium containing a predetermined quantity of a lymphokine. Preferably, the culture medium is LAK medium containing 1,000 u/ml of recombinant interleukin-2 (Amgen Company, Cetus Company, or Immunex, Inc.); and culturing the mixture of lymphocytes in this medium preferably using T75 flasks at 370° C. for approximately 24–72 hours. LAK medium is RPMI-1640+10% heat inactivated human serum+such antibiotics as are deemed necessary, preferably penicillin and streptomycin. Most optimal is an incubation time of approximately 48 hours in order that an early stage LAK culture be produced.

It is conventionally recognized that LAK cell cultures may be prepared and produced using a variety of alternate methods. Other lymphokines, especially those which promote the activation and/or growth of T cells, also may be employed. These may be added at the time of or, alternatively, may be added after establishment of the culture. Although interleukin-2 is most preferred for use as a lymphokine of choice, any conventionally recognized lymphokine (such as those listed within Table III) which activates and supports the growth of T cells may be employed in varying concentration for this purpose by the user as his needs or convenience dictates. Moreover, other conventionally known T cell activation methods (such as the use of lectins, mixed lymphocyte reactions, and mitogenic monoclonal antibodies to the CD3 complex or to the $\gamma\delta$ TCR complex), along or in combination with lymphokines produced by recombinant DNA methods or in conditioned media, may also be employed herein for this purpose.

Similarly, the preferred concentration of T cells, the preferred concentration of lymphokine, and the lymphocyte supporting culture medium are all matters of personal choice which may be varied greatly from the procedure described herein; and may be altered as desired or required to meet specific circumstances and conditions of use. Accordingly, none of these compositions, parameters, concentrations, or choices of culture medium are controlling or of major importance. The sole essential requirement and goal is that the mixture of lymphocytes be maintained in a culture medium containing a measurable quantity of at least one T cell growth supporting lymphokine which results in the activation of T cells generally including such specifically adherent $\gamma\delta$ receptor T cells as may be present in the mixture.

It will be recognized and appreciated also that if the source of lymphocytes is a tissue sample containing activated and/or lymphokine altivatable T cells rather than peripheral blood or lymphoid tissue, preparation of activated lymphocytes proceeds in a parallel manner. For example, in the case of TIL cells prepared from tumor samples, either minced tumor sample or a single-cell preparation from the tumor sample (Topalian et al., *Jour. Immunol. Methods* 102:127 (1987); Kurnick et al., *Clin. Immunol. Immunopathol.* 38:367 (1986)) is incubated in LAK medium containing one or more lymphokine(s)—at least one of which will support the growth of T cells and is preferably IL-2.

Early TIL cultures (i.e., actively growing cultures which have expanded to a number of cells which is practical to work with by these methods—about $10^7$–$10^8$ lymphocytes) may then be used to isolate specifically adherent T cells by the earlier described method used for preparing LAK cultures derived from peripheral blood. However, unlike the case of peripheral blood lymphocytes, there is no need for a plastic adhesion step to remove macrophage/monocytes (which are few in number and at least in some ways may be necessary for activation of TIL cells); and the cells resulting from this latter procedure usually contain much fewer NKs, and in fact are often >90% CD3+ T cells.

C. Incubating the Activated Lymphocytes in the Presence of at Least One Extracellular Matrix Protein The prepared culture of activated lymphocytes (whether a LAK culture prepared from peripheral blood or lymphoid tissue; or a TIL culture; or another preparation of tissue infiltrating lymphocytes) is then suspended and incubated within a lymphocyte supporting culture medium containing a lymphokine which supports T cell growth and in the presence of a protein coated solid surface in which the protein coating comprises at least one basement membrane protein. For purposes of convenience and ease, it is most desirable that the internal surface of the multiwell culture plate or the internal wall surfaces of the culture vessel be employed as the solid support substrate upon which the protein coating is applied. Alternatively, any other solid material which provides a surface which can be coated with a basement membrane and then submerged in the culture medium may also be used as desired or required. Presuming the use of a single or multiwell plastic plate as the culture vessel (preferably a non-tissue culture treated plastic petri dish such as a Falcon 1007 dish), it is required that the internal surface be coated with at least one extracellular matrix protein as these are conventionally known in composition and structure. Suitable extracellular matrix proteins include but are not limited to all forms of collagen including collagen IV; laminin; heparin sulfate proteoglycans; nidogen/entactin; BM-40 (also known as SPARC or bone osteonectin); glycoaminoglycans; and fibronectin. Alternatively, one may use solubilized, multicomponent extracts of whole basement membrane (such as Basement Membrane Matrigel TM sold by Collaborative Research, Inc., which is prepared from the basement membrane of the Engelbreth-Holm-Swarm murine tumor) or crude extracellular matrix preparations. One would coat the plastic plates with thin gels of this extract material (i.e., Matrigel) as per manufacturer's direction; and then dry the gel material overnight on the plate as for the purified proteins. The chemical composition and structure of basement membranes are conventionally known and represented by: Martin, G. R., *Ann. Rev. Cell Biol.* 3:57-85 (1987) and the reference cited therein. The interactions of certain tumor cells with basement membranes and their components are also conventionally known. The interactions of nerve cells, endothelial cells, and hematopoietic precursor cells in bone marrow are active areas of research. However, the interaction of T cells, and in particular $\gamma\delta$ T cells with basement membrane components or with other extracellular matrix components is previously unknown and unappreciated in this art.

Most preferred for use as a protein coating on the solid wall surface of the culture vessel is collagen IV (Collaborative Research, Inc.). The native murine collagen IV was prepared from the basement membrane of the Engelbreth-Holm-Swarm tumor by the method of Kleinman et al., (*Biochemistry* 21:6188 (1982)). Note that only native collagen IV, and not the denatured form will bind laminin. Preferably collagen IV has been prepared by dissolving the material in sterile 0.1 M acetic acid at a concentration of 100 µg/ml; and then poured onto the internal surface of the culture vessel and allowed to dry. In addition, it is desirable to increase the specificity of cell adhesion by taking the prepared collagen IV (or other basement membrane protein) coated plates and subsequently treating each collagen IV protein surface with 1% bovine serum albumin to reduce non-specific binding. In the alternative, it is expected and intended that any of the other conventionally known basement membrane or other extracellular matrix proteins may be employed in place of the preferred collagen IV protein in these procedures.

For purposes of the present invention, the prepared activated lymphocytes may be suspended and incubated in any lymphocyte supporting culture medium which preferably contains a useful concentration of a lymphokine which supports T cell growth and viability so long as such incubation occurs in the presence of the basement membrane protein coated solid surface (although in particular instances no lymphokine may be required). However, one or more additional basement membrane proteins may be included in the fluid medium with the activated cells; alternatively, these additional proteins may be added as part of the prepared basement membrane protein solid coating or pre-incubated with that solid protein coating prior to adding the activated lymphocytes. Preferably, one uses plates coated with collagen IV as described above and laminin at a concentration of 10 µg/ml mixed in the culture medium. A preferred source of laminin is murine laminin prepared form the basement membrane of the Engelbreth-Holm-Swarm tumor using the method of Ledbetter et al., (in Methods for Preparation of Media, Supplements and Substrata for Serum-Free Animal Cell Culture, A. R. Liss, Inc., New York, 1984, p. 231), commercially available from Collaborative Research, Inc.

Most desirably, the activated lymphocytes are dispersed at approximately $10^7$ cells per plate or well using 3 ml of LAK medium containing 1,000 u/ml of interleukin-2, 200 µg/ml of bovine serum albumin and laminin at a concentration of 10 µg/ml. This amount of laminin appears empirically to be optimal and desirable. This cellular reaction mixture is then incubated for 1-12 hours duration, but preferably for only 2-4 hours incubation, at 37° C. The purpose and result of this incubation interval is to permit at least a portion of the activated lymphocytes to become physically adherent to the solid basement membrane protein coating of the support surface.

D. Isolating The Cell Fraction Adhering To The Basement Membrane Protein Coating The separation and isolation of the protein coating adherent and non-adherent cells may be effected using any conventionally known means so long as there is no substantive damage to that cell fraction adhering to the basement membrane protein coating. Accordingly, one desirable technique removes non-adherent cells by washing the plates extensively with warm LAK medium initially. Then, using Hank's Balanced Salt Solution ("HBSS") without calcium or magnesium metals but including 1 mM EDTA at 4° C., the protein coating adherent cells become detached from the solid protein coating. In this manner, the basement membrane protein coating adherent cells are detached, collected, and preferably subsequently concentrated by centrifugation. This isolated, extracellular matrix protein adherent fraction, if derived from peripheral blood lymphocytes, contains mainly CD3− (presumably NK) cells (between 50%-90%). with the remaining cells being CD3+ T cells. Alternatively, if the lymphocytes are derived from TILs, the activated cells will usually contain fewer NK cells than peripheral blood lymphocytes; and often the extracellular matrix membrane adherent cell fraction derived from these populations will contain few or no NKs at all. The T cell fraction of the isolated adherent cells was found to contain between 25-85% γδ T cells, when collagen IV & laminin were used.

E. Reactivating And Culturing The Isolated Cell Fraction

Subsequent to isolation, these extracellular matrix protein adherent cells are subjected to conventionally known reactivation and culture conditions which supports the growth of T cells. Under these conditions, the NK cells in the extracellular matrix protein binding fraction do not grow and are lost from the culture. The cells are resuspended in conditioned culture medium (i.e.., filtered medium from the initial lymphokine-containing culture of activated lymphocytes from which the selection with basement membrane protein was done), and subjected to conventionally known T cell reactivation methods. After reactivation, the cells are then resuspended in a culture medium containing a lymphokine which supports the growth of T cells, preferably LAK medium plus between 100-1,000 units/ml of IL-2. The cells, starting with about $10^6$ cells recovered from the basement membrane protein selected fraction, will expand to at least $10^{11}$.

The cells may be expanded over time using periodic 1:1 dilutions of lymphokine-containing medium and be maintained at a cell concentration between $5 \times 10^5 - 2.5 \times 10^6$ per milliliter. The culture will then typically contain between 15%-90% γδ T cells; and in cultures containing lower proportions (15%-25%) of γδ T cells, the proportion of γδ T cells appears to increase to at least 40%-50% with continued growth of the culture.

To aid the user in understanding and using the individual methods of the present invention, a detailed protocol for isolating EMATs containing specifically adherent γδ and αβ T cells is provided. It will be understood that the details of the described protocol are those presently considered to be most optimal and desirable for use.

Preferred Protocol

1. Coating of Plates
   (a) Use Falcon petri dishes (not cell culture treated) 60×15 mm style (Falcon No. 1007).
   (b) To each plate, add 3 ml sterile 0.1M acetic acid containing 30 µg collagen IV. (Collaborative Research provides native collagen IV received as 1 mg in 0.05N HCl at 1.32 mg/ml; follow their directions for thawing, etc. Make up solution in 0.1M acetic acid and swirl well.)
   (c) Air dry overnight, in the hood, under the UV lamp. Store, wrapped in Parafilm or taped to seal, at −20° C.

2. Preparation Of Peripheral Blood Mononuclear Cells (Boyum, A., *Jour. Clin. Lab. Invest.* 21 (Suppl. 97): (1968))
   (a) Draw blood (usually 50 cc) from human volunteer donor, using heparinized tube. Expect $1-2 \times 10^6$ PBL/ml blood.
   (b) Dilute blood 2X with HBSS minus Ca/Mg in 50 ml conical centrifuge tubes.
   (c) Transfer diluted blood into 15 ml conicals, 10 ml per tube. Carefully underlayer with 3 ml Ficoll-Hypaque, using a long sterile needle and syringe.
   (d) Centrifuge at room temperature, 20 minutes at 2,000 RPM.
   (e) Aspirate off most of top liquid with a 5 ml pipette. Pipette up PBL layer atop Ficoll medium with a plugged sterile pasteur pipette, using a circular motion, being careful not to dip into the granulocyte/red blood cell layer. Transfer PBL layer to a 50 ml conical and dilute a minimum of 3X with HBSS minus Ca/Mg. (for 50 cc of blood, usually dilute in 100 ml HBSS, 50 ml in each of two 50 ml conicals).
   (f) Pellet cells by centrifugation at 1,500 RPM, 10 minutes; and decant. Rewash cells one to two more times with HBSS without Ca/Mg to remove the platelets. Make a cell count before the last centrifugation.

3. Preparation of Macrophage-Depleted LAK Cultures
   (a) Prepare Ficoll PBL as described in protocol part 2, above
   (b) Remove macrophages (and plastic adherent lymphocytes) by suspending the cells at $10^6$ cells/ml in LAK medium (RPMI $-1640+10\%$ heat inactivated human serum) and incubate in T75 flasks, ca. 10 ml per flask, treated side down, at 37° C.
   (c) Remove supernatant containing non-adherent lymphocytes, and add sufficient IL-2 to prepare a concentration of 1,000 u/ml IL-2. Incubate at 37° C. in T75 flasks (upright) for LAK culture. Incubate for one or two days, etc.

4. Isolation Of Collagen IV Adherent Cells From LAK Cultures
   (a) In order to minimize non-specific binding, preincubate collagen IV plates overnight with 3 ml of 1% BSA in HBSS (minus Ca/Mg); remove BSA solution prior to using the plate.
   (b) Count the cells. Centrifuge the cells and save supernatant, after filtration through a 0.22 $\mu$ filter, at 4° C. or frozen in aliquots, as conditioned medium. Resuspend the pelleted cells at $3.3 \times 10^6$ cells per ml (on the order of $10^7$ cells per plate in 3 ml) in LAK medium $+1,000$ u/ml. IL-2$+200$ mg/ml BSA. Put 3 ml of this cell suspension into each plate.
   (c) Depending on the experiment, one may then add various amounts of laminin (from Sigma or Collaborative Research) to each plate. 10 $\mu$g/ml appears to be optimal for adherence of cells from LAK cultures, but this may be greatly varied, especially with respect to populations which may require to be stimulated by addition of laminin for adhesion to collagen IV.
   (d) Incubate for various times at 37° C. (ca. 2–4 hours is probably optimal).
   (e) Wash plates extensively with warm LAK medium to eliminate non-adherent cells. Adherent cells will appear flat and "blue" under the phase optics of the Nikon Diaphot inverted microscope.
   (f) Incubate cells at 4° C. with 3.0 ml per plate of HBSS (minus Ca/Mg)$+1$ mM EDTA for 20 minutes and pipette to remove the cells. Repeat step if necessary. Remove resuspended cells with a pipette into a 15 ml conical tube and centrifuge cells. Resuspend pellet in 1 ml of conditioned medium (prepared as described in protocol part 4(b), above); count (using 0.2 ml) the cells and culture the remaining cells in a well of a plate. Adherent cells are generally between 1-2% of the culture.

5. Reactivate The Cells
Any of a variety of known activation methods can be used, and examples are outlined in the summary of the invention. The following is presented as an example.
   (a) This step may be achieved by one of two conventionally known methods which will reactivate a broad spectrum of T cells, independent of their antigen specificity:
      (i) Reactivation by mixing the cells with an excess (5–10 fold) number of irradiated peripheral blood mononuclear cells (either autologous or from a heterologous donor) together with a T cell stimulatory lectin such as phytohemagglutinin (PHA) at a concentration of 1 $\mu$g/ml (William et al., Jour. Immunol. 133:2986 (1984); Brenner et al., Nature 325:689 (1987));
      (ii) Reactivation by monoclonal antibodies which are mitogenic for T cells. Such antibodies are specific either for CD3 (in which case they will reactivate all classes of mature T cells); or they are specific for various classes of TCR proteins themselves, in which case they will reactivate only T cells bearing those classes of T cell receptors for which they are specific. In the absence of accessory cells such as macrophages, these antibodies must be bound to a solid surface, such as the plastic well of a tissue culture plate, in order to give reactivation of the cells. This is exemplified by the work of Rivas et al. (Jour. Immunol. 142:1840 (1989)) who reactivated $\gamma\delta$ T cells using cell culture wells which had first been coated with goat antimouse immunoglobulin G (IgG) antibody in order to efficiently bind mouse anti-human CD3 antibodies to the surface of the well; and then subsequently treated with either of the anti-CD3 antibodies OKT3 (Ortho) or Leu4 (Becton-Dickinson). The cells were then added to the wells in IL-2 containing medium.

Reactivation of the cells (in some cases) may have to be repeated about one week later, in order to achieve long-term continuous growth of the culture. Once this has been accomplished, expansion of cultures isolated from 50 cc of blood from normal human volunteers to levels equal to or greater than $10^{11}$ cells have been achieved.

(b) Culture the Reactivated Cells. As cells expand, dilute 1:1 with LAK medium$+100$–1,000 u/ml IL-2.
   (c) Optional further purification methods for $\gamma\delta$ T cells may then be performed. The above method will yield a growing population containing between 15%–90% $\gamma\delta$ T cells. Moreover, in populations which have lower numbers of $\gamma\delta$ T cells (ca, 15%–25%) early after reactivation, the proportion of $\gamma\delta$ T cells in the culture appears to increase with subsequent growth to at least 40%–50%. If, especially for investigational use, one requires pure specific adherent $\gamma\delta$ T cells, or pure specific adherent $\alpha\beta$ T cells, conventionally known methods including the following may be employed:
      (i) Panning (Wysocki and Sato, Proc. Nat. Acad. Sci. 75:2844 (1978)): This method using anti-TCR$\delta$1 as the specific antibody involves attachment of the specific antibody to a plastic plate; and uses the antibody to specifically bind those cells which have surface proteins for which the antibody is specific. Alternatively, one may use anti WT31 antibody (negative selection) to remove T cells. The opposite applies, as will be appreciated, where specific adherent $\alpha\beta$ T cells are desired.
      (ii) Negative selections via antibody and complement treatment (Cacy et al., Proc. Nat. Acad. Sci. 86:1023 (1989)): Cells are treated with a complement-fixing antibody against $\alpha\beta$ T cells if available; or a non-complement fixing murine monoclonal antibody (such as WT31) followed by a complement-fixing antimurine antibody. This is followed by treatment with rabbit complement; cells to which the antibody has been bound will be killed by the complement. Dead cells are then removed by centrifugation through Ficoll Hypaque. This method may be combined with panning for more complete purification. The cells may then be reactivated and cultured. If αβ T cells are desired, complement-fixing anti-γδ should be used, as will be appreciated.

(iii) Cloning by limiting dilution (Patel et al., *Jour. Immunol.* 143:1108 (1989)): In wells using irradiated autologous peripheral blood mononuclear cells in the presence of PHA as feeders (in IL-2 containing medium), and testing clones for positive staining with anti-TCRδ1 or anti-WT31, respectively. This method will give purified clones of γδ and αβ T cells, the properties of each of which may be investigated. This method thus differs from panning, negative selection with antibody/complement, or use of reactivated and cultured basement membrane adherent T cells without further purification, since all three of the later protocols yield bulk, polyclonal populations of cells, which consist largely or entirely of γδ T cells, or of αβ T cells, if the appropriate reagents are employed, as will be appreciated.

Cell cloning can also yield purified clones of adhesive (i.e., "EMAT" phenotype, as described more fully below) αβ T cells, which can also be useful.

V. Characteristics of the Extracellular Matrix Membrane Protein Adherent T Cell Lymphocytes Isolated According to the Invention The cell fraction able to bind to collagen IV/laminin protein coatings is about 1–4% of the number of lymphocytes present in two day old LAK cultures prepared from normal human peripheral blood. The binding of these cells to an extracellular matrix protein appears to take place in four hours or less under the conditions of the preferred protocol. Similarly, the binding to collagen IV/laminin was found to be between about 60–85% specific as compared to non-specific binding to untreated plastic plates with cells obtained from LAK prepared cultures. In general, the isolated adherent cell fraction, if derived from peripheral blood lymphocytes, contains mainly CD3$^-$ (presumably NK) cells (between 50%–90%), with the remaining cells being CD3$^+$ T cells. In the case of Collagen IV/laminin adherent cells derived from peripheral blood, the T cell fraction contains between 25%–85% γδ T cells. After reactivation and culture, the growing cell population has been found to contain over 90% T cells, of which between 15%–90% are γδ T cells. Both αβ and γδ T cells are at least largely specifically adherent, as described below. In comparison, the binding to collagen Iv/laminin of activated lymphocytes derived from other sources, including TILs, is highly variable. TILs usually contain fewer NK cells than peripheral blood lymphocytes (and often contain little or no NKs), so the basement membrane adherent cell fraction derived from these populations will contain fewer or no NKs).

Within the isolated and cultured T cell population, the cells were either CD4$^-$ CD8$^-$ (double negative) cells, or CD4$^-$ CD8$^+$. When one of these populations was tested with the anti TCRδ1 antibody which is specific for a common epitope of the delta receptor protein in the γδ T cell receptor, 80% were found to stain delta (δ) positive. It is clear that the majority of the double negative and the CD8$^+$ T cells in this isolated population bear γδ receptor proteins. In addition, these cells were found to be cytotoxic for both K562 cells (a NK-sensitive tumor cell line) and Daudi cells (a NK-resistant tumor cell line).

To further empirically document and confirm these observed characteristics, a series of individual experiments was performed as are described hereinafter. The purpose of this empirical description and data is merely to further demonstrate the representative membership of the T cell lymphocyte population isolated and cultured collectively by the methods of the present invention. It will be expressly understood and recognized that the experiments and/or empirical data are merely representative of the present invention as a whole; and do not in any manner serve to limit or restrict the as present invention to either the experimental design or the empirical results presented.

VI. Useful Properties of Basement Membrane Protein Adherent γδ T Cells Isolated According to the Invention and their Therapeutic Applications

Properties

1. Gamma/delta T cells, which constitute a minority of T cells in peripheral blood and lymphoid organs, appear to demonstrate localization in tissues. In the mouse, particular narrow classes of γδ T cells have been shown to localize in the skin and intestinal epithelia. Although no such localization in normal tissues has been found in the human, human γδ T cells appear to localize in various inflammatory sites in the tissues. Gamma/delta T cells are reported to localize around high epithelial venules of lymph nodes; these have the following attributes of blood EMATs: they are associated with basement membrane, they have an amoeboid morphology, and they belong to the δTCS1$^-$ subgroup of γδ TCR.

2. Populations of γδ T cells isolated by the preferred protocol and activated by IL-2 can bind to collagen IV in the presence of laminin. These cells are extracellullar matrix adherent T cells and are thus called "EMAT" cells. Collagen IV and laminin are the major components of basement membranes which provide support, boundaries, and often essential growth and differentiation stimulation for capillary endothelial cells and epithelial cells in most tissues in the living body. Capillary endothelial cells and their associated basement membranes, as well as basement membranes associated with other tissue components, also constitute in vivo barriers to penetration of T cells, other immune cells such as B-cells, macrophages, and granulocytes, and of tumor cells. Many cells which bind to basement membranes can also penetrate these barriers in vivo. For studies on relationships between binding to basement membrane components and invasion of tissues by metastatic tumor cells, see R. H. Kramer et al., *Int. Jour. Cancer* 26:639 (1980); and V. P. Terranova et al., *PNAS* 80:444 (1983).

Activated EMATs bind to basement membranes. The penetration of endothelial cells of capillaries and venules, and especially of high endothelial venules, may be restricted to capillaries either in areas of inflammation (including tumors); damaged blood vessels (i.e., blood vessels which display naked basement membranes—including deranged blood vessels in many solid tumors); or capillaries and venules in areas of the body for which the EMAT cells have specific homing receptors. See for example, A. Duijvestijn and A. Hamann, *Immunology Today* 10:23 (1989); Yednock and Rosen, *Adv. Immunol.* 44:313 (1989); and Stoolman, *Cell* 56:907 (1989) for reviews of lymphocyte homing, recirculation, and known and postulated roles for adhesion molecules in tissue and organ-specific homing of lymphocytes. Note also that special classes of murine γδ T cells which are found in specific tissues appear to home specifically to those tissues, although the precise mechanisms for this homing phenomenon or any relationship for the role of adhesion molecules in tissue-specific homing of lymphocytes is as yet unknown. In addition to cells in the peripheral blood, there are γδ T cells in epithelial tissues, in inflammatory sites, and (as demonstrated herein) among tumor infiltrating lymphocytes in vitro. The latter, under the proper culture conditions and isolation methods, can be isolated from in vitro cultured TILs.

3. Almost all activated γδ T cells which have been empirically assayed demonstrate cytotoxicity for allogeneic and in at least some cases, syngeneic tumor cells; and in one case the cells are highly specific for B cell lymphomas, namely specific for an idiotypic determinant of surface immunoglobulin. The syngeneic case is one in which double negative (and therefore presumably γδ T cells from the peripheral blood of melanoma patients have also been found among T cell mixtures which become activated when exposed to melanoma cells from the same patient (P. Hersey et al., *Cancer Immunol. Immunother.* 22:15 (1986)). Cytotoxic activity of γδ T cells includes non-specific LAK-like activity; and, at least in some cases, cytotoxic activity which may be specific for certain MHC proteins (Bluestone and Matis, *Jour. Immunol.* 14:21785 (1989)). LAK-like cytotoxic activity for EMAT cells has been empirically demonstrated.

Extracellular Matrix Adherent T Cell Populations Enriched for TCR γδ Cells

Receptors that mediate interactions of cells with extracellular matrix (ECM) proteins are of key importance in localization and function of many types of cells (see, Ruoslahti and Pierschbacher, Science 238: 491–497, 1987; Hynes, Cell 48: 549–554, 1987; M. E. Hemler, Annu. Rev. Immunol. 8: 365–400, 1990). Recent work indicates that this is true for cells of the immune system. Savagner et al., Jour. Cell Biol. 103: 2715–2727, 1986, describes blocking of migration of avian precursor cells into the embryonic thymus by antibodies against fibronectin, laminin, and the $\beta_1$ chain which is common to the "very late antigen" ("VLA") subfamily of integrin adhesion receptor molecules, and also by the peptide arginine-glycine-aspartic acid-serine ("RGDS"). This indicates that this migration is in part dependent upon integrins which are receptors for the ECM proteins fibronectin and/or laminin, and which recognize RGD sites on these proteins. ECM interactions may also be important in later development of T cells within the thymus; Cardarelli et al., PNAS 83: 2647, 1986, and Cardarelli et al., 1988, Jour. Cell Biol., 106:2183 describe adherence to fibronectin by about 10% of murine thymocytes, largely of CD4− CD8− and CD4+ CD8+ immature phenotypes.

Receptors for ECM proteins have also been implicated in migration and function of mature T cells. In particular, the integrin VLA-4, described by Wayner et al., J. Cell Biol. 109: 1321–1330, 1989, and Guan et al., Cell 60: 53–61, 1990, to be a receptor for a non-RGD peptide sequence in the heparin binding CS-1 domain of fibronectin, is described by Elices et al., Cell 60: 577–584, 1990 to be a receptor for a distinct molecule, vascular cell adhesion molecule-1 (VCAM-1). VCAM-1 is expressed on the surface of cytokine-activated human endothelial cells, and may mediate adhesion and entry of lymphocytes into extravascular tissues at site of inflammation (see, Osborn et al., Cell 59: 1203–1211). Holzmann et al., Cell 56: 37–46, 1989, and Holzmann et al., EMBO Jour. 8: 1735–1741, 1989 identify a molecule which appears to be the murine analogue of VLA-4 and a variant form of murine VLA-4 known as VLA-4P as homing receptors which mediate adhesion to high endothelial venules (HEV) in Peyer's patches and entry into the mucosal lymphoid organs in the intestine. In addition, the non-integrin receptor CD44 has been implicated by Jalkanen et al., J. Cell Biol. 105: 983–990, 1987, and Haynes et al., Immunol. Today 10: 423–428, 1989 as one of the receptors involved in homing to peripheral lymph nodes and mucosal lymphoid organs via high endothelial venules (HEV) in the mouse and the human, and by Carter et al., J. Biol. Chem. 263: 4193–4201, 1988 in adhesion to the ECM proteins collagen and fibronectin. Thus the same proteins on the surface of T cells which are receptors for ECM may also be receptors for cell surface molecules on endothelial cells which mediate localization of the T cells in lymph nodes, mucosal lymphoid organs, and in inflammatory sites.

Mature T cells which bear the TCR γδ have been found to exhibit specific localization and recirculation properties. In the mouse, TCR γδ cells with distinct TCR repertoires have been found to localize respectively in the skin (Asarnow et al., Nature 341: 60–62, 1989, and Asarnow et al., Cell 55: 837–847, 1988), in the intestinal epithelium (Takagaki et al., Nature 339: 712–714, 1989, and Asarnow et al., 1989), and in epithelia of the vagina, uterus, and tongue (Itohara et al., Nature 343: 754, 1990). TCR γδ cells appear to constitute the majority of T cells in these murine epithelia. Moreover, Mackay et al., Jour. Exp. Med. 171: 801–817, 1990 found that a large fraction of peripheral sheep TCR γδ cells preferentially follow the same recirculation pathway (blood to tissues to afferent lymph) as memory T cells. This is different from the recirculation pathway (blood to lymph nodes via high endothelial venules ("HEV") (see, Butcher, Curr. Top. Microbiol. Immunol., 128: 85–122, 1986, and Duijvestijn et al., Immunol Today 10: 23–28, 1989) which is followed by the majority of peripheral blood T cells, which are of naive phenotype.

In humans, however, no exclusive or majority populations of TCR γδ cells have been seen in association with normal epithelial tissue. Neither TCR αβ or TCR γδ cells have been found to localize in normal epidermis, and TCR γδ cells have been found to constitute a small minority of T cells in the normal gut (see, Groh et al., Jour. Exp. Med. 169: 1277–1279, 1989; Bucy et al., Jour. Immunol. 142: 3045–3049, 1989). However, the majority of human gut TCR γδ cells appear to preferentially localize in the intestinal epithelial layer (Bucy et al., 1989). Moreover, TCR γδ cells in human tonsils and peripheral lymph nodes have been frequently seen beneath the epithelia of these organs, and in association with small blood vessels, at least many of which are HEV (see, Fallini et al., Jour. Immunol. 143: 2480–2488, 1989). Therefore, as in the case of the mouse, a fraction of TCR γδ cells appear to localize to structures (epithelial cell layers and small blood vessels) characterized by basement membranes; TCR γδ cells in these locations are indeed frequently seen in association with the basement membranes themselves. However, it is not known whether TCR γδ cells which localize in a particular human organ or tissue have a distinctive, tissue-specific TCR repertoire. The difference between the mouse and the human with respect to TCR γδ cell localization could either be due to differences in migration patterns in TCR γδ cells between the two species, or differences in migration patterns of subsets of TCR αβ cells which specifically localize in epithelial tissues.

The mechanism by which TCR γδ may home to specific tissue sites is unknown. As has been discussed by Itohara et al. (1990), it is unlikely that localization of a particular subset of TCR γδ cells is directly determined by its TCR, since in transgenic mice one can obtain localization in a particular tissue of cells expressing TCR γδ genes which are different from TCR γδ genes normally expressed in T cells found in that tissue (see also, Ferrick et al. Cell 57: 483–492, 1989). An alternative explanation is that specifically homing TCR γδ cells of distinct lineages differ not only with respect to their TCR, but also with respect to homing receptors and perhaps other properties.

I have identified and substantially purified from the peripheral blood of normal human subjects and from an epithelial thymus tumor human lymphocytes that bind to collagen IV in the presence of laminin. T cells in these populations are enriched for TCR γδ cells, and can be expanded to high cell numbers in IL-2 containing media. The cultured T cells exhibit specific adhesion to collagens I and IV and to fibronectin. The high proportion of TCR γδ cells in these extracellular matrix adherent T cell ("EMAT") populations suggests that these cells may constitute subsets of cells with distinctive adhesion properties, which can be involved in localization in specific tissue sites and/or specific trafficking during immune responses. Both γδ T cells and αβ T cells in this EMAT preparation exhibit specific adhesion properties, namely binding to collagen>fibronectin and not laminin or fibrinogen, and can exhibit localization properties.

Phenotypes of Cell Lines Cultured From Collagen/Laminin Adherent Lymphocytes Cell surface markers present on cells of two cell lines cultured from collagen/laminin adherent IL-2 cultured PBL (PW-EMAT and ZB-EMAT) and on cells of the cell line cultured from the collagen/laminin adherent TILs (AKT-EMAT) were determined. Although the initial adherent subpopulations of IL-2 cultured PBL may contain a majority of CD3− cells, at least the vast majority (≧95%) of cells in the cell lines derived from these initial populations are CD3+ TCR+ T cells. T cells thus appear to have a strong selective advantage in the activation and culture procedures employed in the expansion of these cell lines. As in the case of the initial adherent populations, the cultures derived from them are highly enriched for TCR γδ cells. The ratio of αβ to γδ cells, however, is variable with growth and activation conditions, as has been seen with other mixed populations which contain both αβ and γδ T cells. This variability is seen even with the same cell line at different times when frozen samples are thawed, reactivated, and expanded. The cultures usually contain little or no CD4+ cells. However, as shown in FIG. 2, the cultures (especially AKT-EMAT, which is the one TIL derived EMAT) can at times (although rarely) exhibit significant numbers of CD4+ cells, which, however, appear to express low amounts of CD4.

Double staining for CD8 and the TCR reagents WT31 and TCR γδ demonstrated that at least the great majority of αβ T cells were CD8+ and that γδ T cells included both CD8+ and CD4− and CD8− (double negative) phenotypes.

Adhesion to Extracellular Matrix Proteins by T Cells in EMAT Lines

Each of the three EMAT lines tested (PW-EMAT, ZB-EMAT, and AKT-EMAT) showed specific binding to collagen IV, collagen I, and fibronectin, but binding to laminin and fibrinogen was no greater than binding to the control proteins BSA and ovalbumin. Adhesion was approximately equal between collagens IV and I, and greater to the collagens than to fibronectin by a factor of about two.

Since each of the three cell lines are cell mixtures containing both TCR αβ T cells and γδ T cells, it was important to determine which of these two subsets included cells which were adherent to the extracellular matrix proteins. Cells of each of these EMAT cell lines (two PBL-derived, one TIL) which bound both to collagen IV and to fibronectin was found to contain both TCR γδ and TCR αβ fractions. This indicates that both TCRγδ cells and TCR αβ cells in the EMAT population demonstrate specific adhesivity, and that the αβ and γδ subpopulations bind similarly with respect to different extracellular matrix proteins.

Morphology of Cells in EMAT Populations

EMAT populations include cells which exhibit abundant and rapid extension of filopodia, ameboid motion, and adhesion and spreading on cell culture plates. Cells in EMAT populations which adhere to collagens IV and I or to fibronectin also exhibit cytoplasmic spreading, abundant filopodia (in some cases assuming a "neuron-like" form with axon-like cytoplasmic extensions), and rapid, ameboid changes in cell shape.

Method of Isolation

The preferred method of isolation of EMATs involves use of a complex medium, including serum, in addition the use of both collagen IV (bound to the plate) and laminin (in the medium). It is designed to provide any serum factors that may be needed for cell spreading, and is analogous in this respect to methods for isolating minority subpopulations of plastic-adherent cells from IL-2 activated PBL.

I have demonstrated isolation of EMAT from all normal peripheral blood samples tested (6 donors), and from one TIL. However, the majority of neither αβ nor γδ T cells from either the IL-2 activated PBL cultures bind to collagen IV/laminin plates. Moreover, I observed no adhesion to collagen IV/laminin plates in several T cell populations, all of which contain γδ T cells at least as a minority: 1. TIL derived from the second metastasis from the same patient from which AKT-EMAT was isolated. 2. a TIL population obtained from Kurnick's lab, which has been subjected to long term expansion, including several reactivations with feeder cells and PHA.

The adhesive "EMAT" phenotype may be seen in cells of various TCR types, including: 1) αβ (diversity of $v_\beta$ and $v_\alpha$ use unknown); 2) γδ TiγA+ δTCS− (as in PBL-derived EMAT); 3) γδ δTCS+ TiγA± (as in EMAT from AK-TIL). "EMAT" is here taken in a strict sense to refer to cells having the binding pattern collagen IV>collagen I>fibronectin, and not laminin or fibrinogen.

In humans, unlike the mouse, no exclusively γδ T cell population is seen at any site in normal epithelial tissues. This may be owing to a greater number in the human of αβ cells, possibly including αβ EMATs, having specific epithelial homing. Even in the mouse, a presence in the gut epithelial mucosa of both αβ and γδ T cells having a specific phenotype, common to αβ and γδ subsets, has been described. The mechanism (or mechanisms) of localization of these cells, and whether the mechanism is related to ECM and/or other receptors, is unknown.

The EMAT phenotype, as determined by adhesion assay without serum, as described above, includes: unusual, high collagen binding (both collagen I and IV about equal); fibronectin binding; and no specific binding to laminin or fibrinogen.

The nature of receptors on EMATs is unknown. RGD experiments suggest integrins, at least in part. The integrin collagen receptors VLA-1 and VLA-2, commonly found on long-term activated T cells, are not inhibited by RGD peptides. VLA-3 (which may bind to collagen, fibronectin, and laminin) and VLA-5 are inhibited by RGD peptides, and are candidates for receptors involved in the adhesion observed in EMATs, however. New, unknown receptors may also be present.

Morphological Aspects of EMATs

EMATs include T cells that exhibit a high degree of motility and pseudopod formation. In adhesion assays, at least a high proportion of EMATs not only adhere, but also spread and form processes on both collagens and fibronectin. In preliminary panning experiments with TCRδ1 antibody, motile cells in the population include both antibody binding (presumptively γδ) and non-binding (presumptively αβ) cells.

EMATs may represent specific lineages or they may represent a functional category. Memory T cells represent a functional category of cells which exhibit special adhesive properties and integrin-mediated co-stimulation, and also appear to have specific homing properties, at least some of which may be mediated by their receptors for extracellular matrix. Memory T cells are co-stimulated via fibronectin (VLA-5) and collagen, but, unlike in EMATs adhesion, fibronectin co-stimulation in memory T cells is about two to five times that of collagen.

Adhesive properties of EMATs may reflect a presence of receptors which are involved in homing and localization (as suggested by the high proportion of γδ T cells among the EMAT subset), and/or a presence of receptors which are involved in trafficking and localization of already activated cells (as are the cells actually observed here) at a site of action.

Note that for adhesion to collagen IV, at least under the conditions used herein, most T cells clearly do not bind, even long term activated populations (such as for example Kurnick TIL) which one would expect express abundant VLA-1 and VLA-2. At least many PBL T cells, and especially memory T cells, have been reported to bind to fibronectin when acutely activated, i.e., they are said to be transiently adhesive; this is also reported to be true for CD4+ cells on laminin. EMATs are adhesive during a substantially more prolonged period.

Certain transformed T cell lines (i.e., not normal, having lost control of growth and displaying long term continuous growth without need for activation) have been reported to bind to fibronectin. In addition, certain normal murine dendritic epidermal T cell ("DETC") lines which display long term continuous growth under appropriate conditions, which are γδ, have been reported to bind fibronectin. However, these murine cells exhibit a different adhesion pattern from that of EMATs (DETCs bind to fibrinogen>fibronectin>vitronectin, and not to collagen). Prolonged adhesivity to ECM substrates may be related to long term activation. Alternatively, however, maintenance by normal T cells of active adhesivity, via an unknown mechanism, may be a factor in maintaining activation, as binding of ECM substrates by helper T cells has been described as giving an activating signal to the cell. Although adhesivity of ECM receptors may be related to long term continuous growth, the spectrum of ECM substrates to which the cell binds (different for human EMATs and murine DETCs) may be related to which receptors are both expressed and activated.

Extracellular matrix adhesion may be related to expression of receptors, and/or to activation of receptors. But expression alone of receptors is not sufficient for adhesion, as shown by expression of VLA-5 on resting T cells but no fibronectin binding.

"Activation" may involve linkage of the receptors to the cytoskeleton. Such linkage can be involved both in molecular signalling (i.e., activation) and in adhesion and spreading on the extracellular matrix protein layer. As with some other non-T cell systems, the presence of ECM receptors on EMATs may be involved in organizing the cytoskeleton, as differences have been observed in organization of the cytoskeleton in different subsets of γδ T cells; EMATs are adhesive and also have active cytoskeletal activity, both characteristics necessary for spreading on a substrate.

Adhesive T cell types (i.e., EMATs, DETCs, helper T cells) could thus differ from other normal T cells with respect both to expression of receptors (quantitatively and qualitatively) and other components which affect "activation" of the receptors.

In addition to localization, extracellular matrix receptors on T cells may also be mediators of T cell activation. Matsuyama et al. (J. Experimental Medicine 170: 1133-1148, 1989) demonstrated synergy between anti-CD3 antibody and fibronectin (and to a lesser extent, collagen) in stimulating proliferation of resting CD4+ murine PBL. This effect of fibronectin could be blocked by antibodies to CD29 (the $\beta_1$ integrin chain) and by specific antibodies to VLA-5, and by an RGD-containing peptide. Conversely, stimulation of the CD3/TCR complex has been reported to affect the adhesive activity of cell surface integrins. Shimizu et al. (Abstract. FASEB J.: A1018, 1990) reported that acute activation of resting CD4+ human PBL by either crosslinking of the CD3/TCR complex with anti-CD3 or the phorbol ester PMA resulted in strong adhesion of the cells to fibronectin and laminin. Studies with specific antibodies and inhibitor peptides were reported to indicate that adhesion to laminin was mediated by VLA-6, adhesion to fibronectin via its central RGDS (arginine-glycine-aspartate-serine) binding site was mediated by VLA-5, and adhesion to the CS-1 domain of fibronectin by VLA-4. CD3+ human PBL acutely activated with TPA, Con A plus TPA, or Con A plus accessory cells have also been reported to demonstrate adhesion and spreading on fibronectin (Kurki et al., Scand. J. Immunol. 26: 645–652, 1987); unstimulated cells showed less binding and little spreading. Adhesion in this study was inhibited 90% by RGDS peptide and binding was also seen to a proteolytic fragment of fibronectin containing the RGDS cell binding site, so it was likely to be at least largely due to VLA-5. T lymphocytes may express VLA proteins but are reported to demonstrate little or no adhesion to their ECM protein ligands. For example, fresh peripheral blood T cells were found to express substantial amounts of VLA-4, VLA-5, and VLA-6, yet demonstrate little binding to fibronectin or laminin. Treatment of these cells with mitogens, as described above, may affect the adhesive activity of already expressed adhesion receptors in addition to effects on expression.

One case in which expression and activity of adhesion receptors is correlated with altered T cell localization and function is that of memory T cells. Peripheral blood T cells which exhibit strong in vitro proliferative responses to recall antigens have been found to express high levels of the adhesion receptors CD29 and CD44, in addition to enhanced levels of three other adhesion receptors, CD2 and its ligand LFA-3, and the leukocyte integrin LFA-1 (Sanders et al., J. Immunol. 140: 1401–1407, 1988). They have also been reported to express greater levels of VLA-4 and VLA-6 (Shimizu et al., 1990). Memory T cells have also been reported to exhibit enhanced in vitro adhesive behavior as compared to T cells of naive phenotype, including enhanced adhesion to endothelial cells and homotypic adhesion (Pitzalis et al., Eur. J. Immunol. 18: 1397–1404, 1988), and, enhanced adhesion to fibronectin and laminin upon treatment with PMA or crosslinking with anti-CD3 (Shimizu et al., 1990). Migration and recirculation of memory T cells also appears to be different from that of naive T cells. T lymphocytes in inflammatory infiltrates in humans have been found to be largely of memory phenotype (Pitzalis et al., 1988). Studies in sheep (C. R. Mackay et al., J. Exp. Med. 171 801–817, 1990) indicated that naive and memory T cells, respectively, exhibit two distinctive pathways of recirculation between the circulatory and peripheral lymphatic systems. Naive T cells appear to follow the well-known recirculation pathway from blood to peripheral lymph nodes, presumably via high endothelial venules (HEV) in the lymph nodes. (Butcher, E. C., Curr. Top. Microbiol. Immunol., 128: 85–122, 1986; Duijvestijn et al., Immunol. Today 10: 23–28, 1989). Memory T cells, however, appear to recirculate from blood into peripheral tissues. In this connection, most, but not all peripheral blood memory T cells appear to lack the Mel 14/Leu8 homing receptor, which is at least in part involved in adhesion of lymphocytes to HEV leading to migration of the lymphocytes into peripheral lymph nodes (Camerini et al., Nature 342:78–82, 1989; Tedder et al., J. Immunol. 144: 532–540, 1990). The mechanism of migration of memory T cells into peripheral tissues and in particular into inflammatory sites is unknown. However, it is possible that VLA-4 adhesion to VCAM-1 could provide one mode of such migration.

In this connection, Goodman and Lefrancois (J. Exp. Med. 170: 1569–1581, 1990) have recently shown that not only the majority murine intestinal intraepithelial T cell population bearing TCR $\gamma\delta$, but also the minority TCR $\alpha\beta$ population, possess specific phenotypic features of intraepithelial T cells (T. Goodman and L. Lefrancois, J. Exp. Med. 170: 1569–1581, 1990). These features include constitutive cytolytic activity, having a large proportion of cells Thy1$^-$, and expression on a large proportion of cells of the leukocyte common antigen (T200)-associated carbohydrate differentiation antigen, T200. The Thy$^-$ and CT1$^+$ phenotypes are not seen with other peripheral T cells, and may reflect the effect of the intestinal milieu on T cell function and/or specific "IEL" (intraepithelial lymphocyte) lineages of $\alpha\beta$ and $\gamma\delta$ T cells which specifically home to the intestinal mucosa and carry out specific functions within the milieu. If the latter is the case then the difference between mouse and human IEL may mainly be a quantitative one, reflecting a higher proportion of TCR $\alpha\beta$ IEL than in the case of the mouse. In the case of mouse or human TCR $\alpha\beta$ intestinal IEL, these cells could also possess the homing receptors and other function-specific phenotypic markers of TCR $\gamma\delta$ cells with similar localization and functional properties.

One type of TCR $\gamma\delta$ T cell with specific localization properties also appears to possess distinctive ECM adhesion properties (Maxfield et al., J. Exp. Med. 169: 2173–2190, 1989). Cultured lines of murine dendritic epidermal T cells (DETCs), the TCR $\gamma\delta$ cells which specifically localize to skin, exhibit adhesion to fibronectin, fibrinogen, and vitronectin. This binding can be blocked both by RGDS and specific monoclonal antibodies to a dimeric protein with a structure which resembles members of the integrin family. As discussed both by Maxfield et al. and Hemler (1990), in structure and ECM specificity, this protein resembles a $\beta_1$ integrin, and may be a known or new member of this family. The protein is also expressed on murine splenic T cells very late after stimulation with Con A (similar to VLA-1 and VLA-2); however no adhesion to ECM of T cells other than DETCs mediated by this protein has yet been reported. Adhesion to ECM proteins of DETCs mediated by this receptor could therefore be involved in the trafficking and/or function of DETCs.

Isolation of Cells From IL-2 Cultured PBLs Which Adhere to Collagen IV Plates in the Presence of Laminin Initial experiments were designed to define conditions under which a fraction of IL-2 cultured PBLs would adhere to collagen IV coated plates. In cells cultured in IL-2 containing medium for 1–2 days, such adhesion, in laminin containing complete medium, appeared to be complete within 2–4 h. The extent of adhesion appeared to be greater in 2 day than in either 1 or 3 day cultures. Adhesion of day 2 cultured PBLs to collagen IV coated plates in the presence of 10 μg/ml laminin varied from about 1–5% of the total cells with PBLs cultured from different normal donor blood samples, while adhesion to uncoated plates was generally 0.5% or less. Adhesion to collagen IV coated plates in the absence of laminin was low; 10 μg/ml laminin appeared to be optimal and was found to increase adhesion to collagen IV plates 2–4 fold. Adhesion to laminin-coated plates (in the absence of collagen IV) or to untreated plates in the presence of 10 μg/ml. laminin was no more than that to untreated plates in the absence of laminin.

Analysis of the Surface Marker Phenotypes of PBLs Which Are Adherent to Collagen IV/Laminin Plates Adherent cell populations isolated from different normal donor blood samples were found to consist of variable proportions of CD3$^+$ and CD3$^-$ cells (between 35-55% CD3+ in three experiments). T cells present in these populations contained a high proportion of TCRδ1+ cells (between 25-85%), as assessed by staining with the pan-TCRγδ antibody TCRδ1, described above. Although the proportion of T cells bearing TCRγδ in the adherent sub-population was high in the three experiments performed, only between 5-10% of total TCRγδ cells in the input population adhered to the plates. Between 0.5-2% of total CD3+ cells were found to be adherent.

Because the number of cells adhering to collagen IV/laminin plates was low, and because populations cultured from the adherent cells were found to consist entirely of T cells, the phenotypes of the CD3− adherent cells were not characterized further. However, results from one experiment (data not shown) suggest that at least a large fraction of the CD3− may be NK cells. When PBL were treated with antibodies to the NK marker NKH1A and CD16 and complement prior to culture in IL-2, the number of cells in the day 2 culture which adhered to collagen IV/laminin plates was reduced by a factor of about two as compared to a parallel culture derived from non-antibody treated cells. The CD3− and total CD3+ fractions of adherent cells were also reduced by about a factor of two; however, the TCRδ1+ fraction was only reduced by about 20%. This indicates that in this culture, a large fraction of both the CD3− cells and the CD3+ cells which did not express TCRδ1 expressed one or both of the markers Leu19 and CD16, while a smaller proportion of the TCRδ1+ cells did so. Note that EMATs have been demonstrated from all 6 normal donors examined.

Expansion of Collagen IV/Laminin Adherent PBLs in IL-2 Containing Media

Although we have observed spontaneous long-term growth of cultures isolated from two collagen/laminin adherent cell populations isolated from PBLs of normal donors (one of which is the cell line PW-EMAT), in most cases only limited expansion is achieved without reactivation of the cells using PHA and irradiated feeder cells. However, once rapid growth is achieved, the cells were found to expand 4-5 orders of magnitude over as long as 4-6 weeks, without a need for further periodic reactivation. This is illustrated for example by the cell line ZB-EMAT, which required two rounds of reactivation before it gave long-term, continuous expansion.

Therapeutic Applications

ECM binding cells isolated and cultured using the present methods from IL-2 activated PBL mixtures can be infused into cancer patients as with LAK or TIL adoptive immunotherapies. EMAT cells are expected to make IL-2 and also may require less IL-2 than with LAK cells, thus reducing the severity of the IL-2 side-effects of treatment (Rosenberg et al., *N. Engl. Jour. Med.* 319:1676 (1988)). Alternatively, EMATs, as with TILs and other T cells, could be grown in low-dose IL-2 supplemented with IL-4, which is expected to result in their ability to grow after infusion into patients with administration of low dose, subtoxic levels of IL-2 (Kawakami et al., *Jour. Exp. Med.* 168: 2183 (1988)). In the extreme case, EMAT cell IL-2 production could suffice to maintain their viability and activation. One would then not need to infuse IL-2 into patients thus making treatments less expensive; eliminate most major IL-2 undesired side-effects; and even make possible outpatient treatment in many cases. The latter also is expected to be facilitated if EMAT cells are indeed more effective per unit than LAKs or TILs, thereby reducing the numbers of cells needed for treatment.

When EMAT cells are infused into patients, being T cells, they are expected to migrate into the spleen, liver, and the lymph notes; with less trapping in the lungs and liver than with LAKs. Indeed, γδ T cells are generally seen to reside in spleen and lymph nodes normally. It is expected that EMAT in the lymph nodes will be able to transit endothelial cell layers and basement membranes in the local circulation and enter the surrounding tissues. In those lymph nodes which are within the local region of neoplastic tumors, this facilitates the entrance of EMAT cells into the substance of the tumors. Location of tumors by EMAT cells which have entered the neoplastic tissues is expected to be facilitated by the well-known phenomenon of breakdown of basement membranes by metastatic tumors (G. Marin and R. Timpl, *Annu. Rev. Cell Biol.* 3:57 (1987)). Cells with receptors for collagen IV and/or laminin have been observed to respond chemotactically to gradients of breakdown products of these basement membrane components (T. J. Herbst et al., *Jour. Cell Biol.* 106:1365 (1988)). Extensive ameboid motion by EMAT cells has been observed—a capability which would fit in and supply the motility needed for these migrations and tumor penetrations.

A second way that EMAT cells are expected to reach tumors in vivo relies upon the phenomenon of angiogenesis (the formation of new capillary blood vessels) in tumors. It has been observed that such tumor infiltrating blood vessels are often disordered, and contain naked basement membrane proteins R. L. Carter, in *Invasion: Experimental And Clinical Implications*, Oxford University Press, 1984, p. 168]. Circulating EMATs are expected to bind to these naked basement membranes; transit them; and thus penetrate the tumor in vivo.

When EMATs enter tumors, they are deemed to carry out a number of anti-tumor activities. The first is cytotoxicity or direct killing of tumor cells. Other cell activities would be dependent on lymphokines and/or other factors such as complement components and leukotrienes being produced by the EMATs cells. One secondary activity would be activation of local capillary endothelial cells. This activity is expected to result in the appearance of new receptors on the surface of these endothelial cells; and then allow for the binding and transit into the tumor of macrophages, neutrophils, and/or αβ T cells which possess homing receptors for the activated endothelial cells involved in inflammation.

A third activity is expected to be activation (via the lymphokines—interferon, GM-CSF, and complement components) of local dendrites and of macrophages which have entered the tumor via the above mechanism. These antigen presenting cells should then process tumor antigens released into the medium via lysis of tumor cells by EMAT cells; and interact with αβ T cells having specificity for tumor antigens sufficient to activate them and induce their proliferation. This, in turn, is expected to result in the growth of new, activated helper and cytotoxic T lymphocytes which will carry out immune activity against the tumor. Increasing infiltrates of macrophages and neutrophils brought in both by the original EMAT cells and perhaps by the helper T cells, being similar to a delayed hypersensitivity reaction are expected to damage local capillaries, resulting in deprivation of oxygen and nutrients to the tumor and lead to massive destruction of the tumor.

In summary, EMAT cells are expected to reach tumors in vivo via transit of the naked basement membranes in the disordered blood vessels induced by the tumors themselves; and/or via transit of intact endothelial venules and/or capillaries in areas of inflammation including tumors, and/or by their own specific homing receptors and capabilities. EMAT cells should then destroy tumor cells via direct cytotoxic activity; and then cause immune initiation and amplification via both their lymphokines and their release of tumor antigens. This also is expected to result in amplified immune reactions mediated by other components of the immune system, notably classical helper and cytotoxic $\alpha\beta$ T cells and macrophages.

Use of EMAT and Other Extracellular Matrix Binding T Cells Exhibiting Long Term Continuous Growth in Gene Therapy In one known "gene therapy" approach, human cancer patients have been infused with TIL transformed with a retroviral vector containing a recombinant drug resistance gene (neoR). Gene therapies involving using, as drug delivery systems, cells transformed with vectors coding for various therapeutic proteins, have been used or suggested for use in treating various conditions, including genetic deficiency diseases (such as ADA deficiency) and other conditions including ones that are not directly caused by mutations, such as, for example, cancer and emphysema. It has been proposed to use such a transformed TIL-based gene therapy approach for treating children with adenine deaminase (ADA) deficiency by infusing each patient with a preparation containing T cells that were isolated from the patient and transformed with a vector carrying a gene for the ADA enzyme.

An ideal cell for systemic gene therapy is a bone marrow stem cell, but these are difficult to isolate and cultivate, and one known approach for treatment of cancer patients uses TILs. An ideal cell for gene therapy of a local condition (including such non-cancer conditions as emphysema, for which the enzyme $\alpha 1$ anti-trypsin is believed to be a therapy), is a cell that can localize to the affected area.

TILs or other mixed T cells are difficult to grow and require reactivation, and for these and other reasons they may not be an ideal T cell to use for gene therapy. EMATs or other extracellular matrix (ECM) adherent T cells, according to the invention, especially those which exhibit long term continuous growth, can be preferable for gene therapies for a number of reasons. They are easier to cultivate. They can localize and distribute more widely (such as, for example, in lymph nodes). They can be longer-lived, because 1) unlike TILs or activated PBL which are largely trapped in liver where they are expected to be mostly destroyed, EMATs and other ECM adherent T cells, if distributed to lymph nodes or other tissue sites, would not be destroyed, and 2) in the case of $\gamma\delta$ EMATs, studies in the mouse suggest that $\gamma\delta$ T cells may be longer lived (at least on the average) than $\alpha\beta$ T cells, and 3) at least many of populations of ECM adherent T cells from a particular source site, these can be expected upon return to the source animal to localize at the source site. Such a treatment using substantially purified ECM adherent cells according to the invention can be used, for example, to localize gene therapy for emphysema.

For use of gene therapies in adoptive immunotherapies for cancer, adhesion-capable T cells, and especially EMATs, can be used for site-directed delivery of, for example, lymphokines (e.g., IL-2, IL-4, GM-CSF), by exploiting their capacity for localization to a site and for controlling, via binding to extracellular matrix protein at the site, expression and production at the site of lymphokines to amplify other immune cells and endothelial cells. Adhesion-capable cells according to the invention that are capable of localizing to a site can be transformed to ensure that they are capable of producing the lymphokines at the site. It has been suggested that binding of CD4 helper T cells (largely memory T cells) can result in expression of the IL-2 gene by the cells. It has also been suggested that binding of murine DETC ($\gamma\delta$ skin T lymphocytes) to fibronectin can result in secretion of GM-CSF or of IL-4 (depending on which DETC clone is used.)

A control region for extracellular matrix binding induction of gene expression in T cells can be used in an expression system to transform an ECM binding T cell to effect ECM binding-mediated induction of lymphokine production by the T cell only at a selected site containing the selected ECM protein. This can provide a particular advantage where the therapeutic substance being used can be lethal to the patient if expressed systemically (such as, for example, tumor necrosis factor, "TNF"), or can have widespread side effects (as, for example, IL-2). Moreover, this control of expression of genes which is dependent on localization and extracellular matrix binding may also be useful in treatment of emphysema (as described above) or other use of gene therapy for treatment of a condition in a local site.

I claim:

1. Substantially purified normal, mature T cells capable of binding in the absence of serum to a collagen, wherein said T cell binds to collagen IV>collagen I>fibronectin, and not to laminin or fibrinogen.

2. A method for increasing the proportion, in a cell population, of normal, mature T cells capable of binding to an extracellular matrix component, comprising steps of providing a cell mixture comprising activated T lymphocytes in a medium, contacting the activated T lymphocytes with a collagen on a support in the presence of soluble laminin to permit at least a portion of the activated T lymphocytes to adhere to said collagen on said support, and separating said medium from said support together with any cells in said medium not adhering to said collagen on said support, and retaining the portion of activated T lymphocytes that adheres to said collagen.

3. The method of claim 2 wherein the step of providing a cell mixture comprising activated T lymphocytes comprises steps of contacting a cell mixture comprising mononuclear leukocytes including T lymphocytes with a plastic support surface to permit monocytes and macrophages present in the cell mixture to adhere to said plastic support surface, and separating said plastic support surface and any cells adhering thereto from the cell mixture comprising T lymphocytes.

4. The method of claim 2 wherein the step of providing a cell mixture comprising activated T lymphocytes comprises steps of providing a cell mixture comprising T lymphocytes, and activating cells in the cell mixture to produce the cell mixture comprising activated T lymphocytes.

5. The method of claim 3 wherein the step of providing a cell mixture comprising activated T lymphocytes further comprises the step of activating cells in the cell mixture to produce the cell mixture comprising activated T lymphocytes.

6. The method of claim 4 or 5 wherein the cell mixture comprising T lymphocytes comprises cells derived from a first source animal, and said activating step comprises contacting the cell mixture comprising T lymphocytes with lymphocytes derived from a second source animal.

7. The method of claim 6 wherein said lymphocytes derived from said second source animal comprise irradiated lymphocytes.

8. The method of claim 4 or 5 wherein said activating step comprises contacting the cell mixture comprising T lymphocytes with a lectin and with irradiated peripheral blood mononuclear cells.

9. The method of claim 8 wherein said irradiated peripheral blood mononucleocytes and at least a portion of the cell mixture comprising T lymphocytes are derived from the same source animal.

10. The method of claim 8 wherein at least a portion of the cell mixture comprising T lymphocytes is derived from a first source animal, and said irradiated peripheral blood mononuclear cells are derived from a second source animal.

11. The method of claim 4 or 5 wherein said activating step comprises contacting the cell mixture comprising T lymphocytes with a mitogenic antibody.

12. The method of claim 11 wherein said mitogenic antibody comprises a monoclonal antibody.

13. The method of claim 12 wherein said monoclonal antibody is selected from the group consisting of anti-CD2, anti-CD3, and anti-T cell receptor monoclonal antibodies.

14. The method of claim 4 or 5 wherein said activating step comprises contacting the cell mixture comprising T lymphocytes with an extracellular matrix component different in composition from said collagen on said support.

15. The method of claim 4 or 5 wherein said activating step comprises contacting the cell mixture comprising T lymphocytes with mixed B lymphoblastoid cells together with a combination of compositions selected from the group consisting of irradiated heterologous peripheral blood lymphocytes, a lectin, a mitogenic antibody and an extracellular matrix protein bound to a support.

16. The method of claim 4 or 5 wherein said activating step comprises contacting the cell mixture comprising T lymphocytes with a first lymphokine-containing medium.

17. The method of claim 16 wherein said lymphokine in said first lymphokine-containing medium comprises an interleukin.

18. The method of claim 17 wherein said lymphokine in said first lymphokine-containing medium comprises interleukin-2.

19. The method of claim 17 wherein said lymphokine in said first lymphokine-containing medium comprises interleukin-4.

20. The method of claim 16 wherein said lymphokine in said first lymphokine-containing medium is selected from the group consisting of tumor necrosis factor, granulocyte macrophage colony stimulating factor, and $\gamma$ interferon.

21. A method for assessing the likelihood that a mixture of cells contains activated, normal, mature T cells capable of localizing to a site in vivo, wherein an extracellular matrix component is present at the site, comprising contacting said mixture of cells with a collagen on a support in the presence of soluble laminin, under conditions that permit binding to said collagen on said support of T cells that are capable of binding to the collagen, whereby greater binding of T cells to said collagen on said support indicates a greater likelihood that said mixture of cells contains activated T cells capable of localizing to the site in vivo.

22. A collagen binding, normal T cell capable of long term continuous growth.

* * * * *

UNITED STATES PATENT AND TRADEMARK OFFICE
CERTIFICATE OF CORRECTION

PATENT NO. : 5,188,959
DATED : February 23, 1993
INVENTOR(S) : Allan B. Haberman It is certified that error appears in the above-indentified patent and that said Letters Patent is hereby corrected as shown below:

```
Column  5, line 56, delete "ells" and insert therefor --cells--;
Column 13, line 38, after "antigen", insert --. --;
Column 18, line 58, delete "370°" and insert therefor --37°--;
Column 19, line 33, delete "altivatable" and insert therefor--activatable--;
Column 26, line 13, after "the" delete "as";
Column 30, line 60, after "from" insert --J. --;
Column 33, line 40, after "171" insert --: --;
Column 34, line  5, delete "Thy-" and insert therefor --Thyl --;
```

Signed and Sealed this

First Day of February, 1994

Attest:

BRUCE LEHMAN

*Attesting Officer*  *Commissioner of Patents and Trademarks*